(12) United States Patent
Cresens et al.

(10) Patent No.: US 7,081,472 B2
(45) Date of Patent: Jul. 25, 2006

(54) SUBSTITUTED BIS-INDOLE DERIVATIVES USEFUL AS CONTRAST AGENTS, PHARMACEUTICAL COMPOSITIONS CONTAINING THEM AND INTERMEDIATES FOR PRODUCING THEM

(75) Inventors: Erwin Cresens, Scherpenheuvel-Zichem (BE); Yicheng Ni, Herent (BE); Paul Adriaens, Herent (BE); Alfons Verbruggen, Wilsele (BE); Guy Marchal, Blanden (BE)

(73) Assignee: K. U. Leuven Research & Development, Leuven (BE)

( * ) Notice: Subject to any disclaimer, the term of this patent is extended or adjusted under 35 U.S.C. 154(b) by 211 days.

(21) Appl. No.: 10/416,043

(22) PCT Filed: Nov. 7, 2001

(86) PCT No.: PCT/BE01/00192

§ 371 (c)(1),
(2), (4) Date: Oct. 23, 2003

(87) PCT Pub. No.: WO02/38546

PCT Pub. Date: May 16, 2002

(65) Prior Publication Data
US 2004/0053911 A1    Mar. 18, 2004

(30) Foreign Application Priority Data
Nov. 8, 2000 (GB) ................................. 0027249.2
Aug. 28, 2001 (GB) ................................. 0120659.8

(51) Int. Cl.
*A61K 31/40* (2006.01)
*C07D 209/02* (2006.01)
(52) U.S. Cl. ................. 514/414; 514/185; 548/455; 548/402; 548/403; 540/474
(58) Field of Classification Search ............... 548/455, 548/402, 403; 540/474; 514/414, 185
See application file for complete search history.

(56) References Cited

FOREIGN PATENT DOCUMENTS

| EP | 0887348 A1 | 12/1998 |
|---|---|---|
| WO | WO 92/11232 A1 | 7/1992 |
| WO | WO 98/05625 A1 | 2/1998 |

OTHER PUBLICATIONS

Database Crossfile Beilstein, Accession No. XP002192307, vol. 26, No. 6, 1992, pp. 492-496.
Database Crossfile Beilstein, Accession No. XP002192308, vol. 7, 1924, p. 583.
Database Crossfile Beilstein, Accession No. XP002192309, vol. 80, 1959, p. 407.
Database Caplux, Accession No. XP002192310, vol. 19, No. 5, 1982, pp. 193-204.

*Primary Examiner*—Kamal A. Saeed
*Assistant Examiner*—Robert Shiao
(74) *Attorney, Agent, or Firm*—Barnes & Thornburg LLP

(57) ABSTRACT

Metal-complexable substituted bis-indole derivatives comprising the structure shown in formula (I) hereunder: enantiomers and pharmaceutically acceptable salts thereof and metal complexes thereof, wherein L, $R_1$, $R_2$, $R_3$, $C_1$, $C_2$, m, n, p, q and r are as defined in claim 1 for use as constrats agents.

17 Claims, 6 Drawing Sheets bis Gd³⁺ complex, Na salt

SUBSTITUTED BIS-INDOLE DERIVATIVES USEFUL AS CONTRAST AGENTS, PHARMACEUTICAL COMPOSITIONS CONTAINING THEM AND INTERMEDIATES FOR PRODUCING THEM

The present invention relates to a novel class of bis-indole derivatives useful as tools in biochemical, biomedical and medical applications. In particular, the present invention relates to the use of these novel compounds or pharmaceutically acceptable salts and formulations thereof in therapeutic and/or diagnostic applications, in particular as contrast agents for the identification and visualization of tissues and organs. More particularly, certain such compounds are useful for the identification and visualization of necrosis and necrosis related diseases including myocardial and cerebral infarction. The present invention also relates to methods for preparing such bis-indole derivatives, as well as intermediates therefore.

BACKGROUND OF THE INVENTION

A few disubstituted or trisubstituted indole and bis-indole derivatives are already known in the art as having therapeutic activity, as shown by the following brief review. 3,5-disubstituted indoles such as serotonine and melatonine are well known. 2,3-disubstituted indoles wherein the 2- and 3-substituents together form a ring next to the pyrrole ring are known e.g. from U.S. Pat. No. 4,430,269, U.S. Pat. No. 5,811,551 and U.S. Pat. No. 6,147,076. U.S. Pat. No. 5,808,064 further discloses 2,3-disubsbtuted indoles wherein the 2-substituent is a trialkylsilyl or triphenylsilyl group. U.S. Pat. No. 5,877,329 discloses 2,3,5-trisubstituted indoles being useful intermediates in preparing biologically active compounds such as certain lipoxygenase inhibitors. U.S. Pat. No. 5,932,743 discloses 2,3-disubstituted indole-6-carboxylic acids having estrogen agonist activity. U.S. Pat. No. 5,573,999 discloses that 2,4-disubstituted indoles can be prepared from 2-haloanilines and enamines in the presence of a Pd compound (*J. Heterocycl. Chem.* (1987) 24:1555). U.S. Pat. No. 3,954,799 discloses that synthesis of 1,3-disubstituted indoles generally requires the vigorous conditions used by Norland et al., *J. Am. Chem. Soc.* (1960) 82:5143 for the condensation of 2-carboxybenzaldehyde and indoles. U.S. Pat. No. 6,245,761 discloses alkylation of 1,2-disubstituted indoles by way of a Mannich reaction.

With respect to bis-indoles, however, a few disubstituted bis-indoles are already known in the art. A first class of 2,2'-dicarboxylic acid (ester)-5,5'-diindolyl derivatives wherein the indole groups are linked through a single bond, oxygen, sulfur, methylene or ethylene, all being made with yields ranging from 46 to 67% by the cyclization of dihydrazones, are known from the publications of Samsonyia et al. in *Chem. Heterocycl. Compds* (1981) 1:57–61 and *Chem. Heterocycl. Compds* (1982) 3:348–351. Additionally, Chemical Abstracts (1961) 55:5457 discloses making 2,2'-dicarboxylic acid (ester)-3,3'-diindolyl sulfide with a 40% yield by reacting $SOCl_2$ with indole-2-carboxylate. *Chem. Heterocycl. Compds* (1978) 2:217–224 discloses making 2,2'-dicarbethoxy-3,5'-diindolyl with a yield of 35% by the cyclization of a hydrazone.

EP-A-887.348 additionally discloses substituted [bis-indol-3-yl)methyl] benzenes wherein the phenyl group of the indole linking bridge is substituted with hydroxy or carboxy, and wherein the phenyl rings of the indole groups are symmetrically substituted in the 5-position or 6-position with hydroxy, bromo, amino, methylamino, diethylamino, isopropyl or ethylthio, these compounds being useful as antitumor and antimetastatic agents. The same document also discloses another type of disubstituted bis-indole, namely 2,3-dihydroxy-1-[bis(2-hydroxyindol-3-yl)methyl] benzene. These compounds can be prepared by condensing benzaldehyde with at least two equivalents of a substituted indole.

International patent application published as WO 98/50357 discloses a group of 5,5'-disubstituted- or 2,2'-disubstituted- or N,N'-disubstituted-3,3'-diindolylmethanes being useful as antiestrogens. In particular there are disclosed 2,2'-di($C_1$–$C_5$)alkyl-3,3'-diindolylmethanes, 1,1'-di($C_1$–$C_5$)alkyl-3,3'-diindolyl-methanes, 5,5'-dihalo-3,3'-diindolylmethanes, 5,5'-di($C_1$–$C_5$)alkyl-3,3'-diindolyl-methanes and 5,5'-di($C_1$–$C_5$)alkoxy-3,3'-diindolylmethanes. They can be obtained by condensing formaldehyde with commercially available substituted indoles, although this has the disadvantage of forming by-products which complicate purification of the desired product. Therefore a preferred synthesis in three steps consists of first forming a substituted indole-3-aldehyde, then reducing it into the corresponding substituted indole-3-methanol which is then condensed for example by treatment with a phosphate buffer having a pH around 5.5.

International patent application published as WO 00/09169 discloses a class of labeled non-porphyrin compounds being e.g. applicable as diagnostic agents in Magnetic Resonance Imaging applications or nuclear medicine, these compounds comprising (i) an agent suitable for targeting a specific organ and/or tissue and comprising one or more organic ring compounds, (ii) an agent suitable for labeling the targeted organ and/or tissue, and optionally (iii) a spacing agent arranged between the targeting agent and the labeling agent. Primarily described in the latter document are pamoic acid derivatives, i.e. compounds wherein the labeling agent and optionally the spacing agent are in β position with respect to the linking agent. Some of these compounds, such as the gadolinium complex of a bis-diethylenetriaminepentaacetic acid pamoic acid derivative obtained from 3-hydroxy-2-naphtalene methyl carboxylate through its reaction with hydrazine, exhibit a unique targetability to necrotic tissues. Such pamoic acid derivatives however exhibit some shortcomings. First, solutions of these compounds with concentrations useful for medical applications are not colorless and, during long term storage, may encounter significant discoloration of pharmaceutical preparations containing them. For instance, a 0.25 mmolar solution of the said gadolinium complex of the bis-diethylenetriaminepentaacetic acid pamoic acid derivative obtained from 3-hydroxy-2-naphtalene methyl carboxylate has a yellow-orange color and has an absorbance of 0.75 at 400 nm. Secondly, despite their relatively high $LD_{50}$ values, significant side effects (e.g. myocarditis) were observed in animals having received an intravenous bolus injection of 1 mmole of the said gadolinium complex per kg body weight.

As a summary, the state of the art provides six different classes of disubstituted bis-indoles, being respectively the symmetrical 1,3-disubstitution, 2,3-disubstitution, 2,5-disubstitution, 3,5-disubstitution and 3,6-disubstitution and the disymmetrical 2,2',3,5'-substitution of a bis-indolyl basic structure. In addition to the said six classes actually disclosed in the art, 1,2- and 2,4-disubstituted indoles are also respectively available, which could in principle be condensed, using coupling procedures standard in the art, in order to achieve the corresponding disubstituted bis-indoles. However, with very few exceptions, the bis-indoles bearing carboxylic acid ester substituents described so far are either symmetrical 2,5disubstituted bis-indoles or the disymmetrical 2,2',3,5'-substituted bis-indoles.

In view of the prevalence of cerebral and myocardial infarction and of other necrosis related phenomena, It would be of great importance to provide contrast agents, in particular multipurpose contrast agents and tissue-specific contrast agents which would be in vivo effective for the identification, localization and therapeutic follow-up of pathological tissue disorders, in particular those resulting from ischemic diseases and space-occupying lesions, including necrosis, but which would not suffer from the above-mentioned drawbacks (significant discoloration upon long-term storage, myocardial toxicity) of the pamoic acid derivatives known in the art. There is also a need in the art for pharmaceutical compositions including tissue-specific and/or multipurpose contrast agents which are suitable for use in magnetic resonance imaging and nuclear scintigraphy imaging technologies while requiring only low doses of the active agent. It is therefore the goal of the present invention to provide useful compounds meeting these various criteria, as well as a suitable and cost-effective manufacturing route for their synthesis.

SUMMARY OF THE INVENTION

Thus viewed from one aspect, the present invention provides new and useful compounds having one of the formulae (I), (Ia) and (Ib) as specified hereinafter, as well as methods for making them. The compounds of general formula (I) are useful as vectors and agents in therapy and medical diagnosis. Viewed from a further aspect, the invention provides compositions, use and methods for use comprising the compounds having formula (I).

The present invention is mainly based on the unexpected finding that useful metal-complexable compounds may be obtained by first preparing 2,3-disubstituted bis-indoles starting materials preferably bearing at least one carboxylic acid reactive substituent (such as acid, acid halide or acid ester) that is able either to directly condense with at least a suitable chelating agent or to react with a spacing agent such as a bis-amine or an amino-acid in order to achieve precursor compounds such as bis(indolecarboxylic acid hydrazides and analogues thereof which themselves are able to condense with at least a suitable chelating agent. The substituted bis-indole derivatives thus produced, as well as their enantiomers and their pharmaceutically acceptable salts, are able to form complexes with radioactive and non-radioactive metals. The metal-complexable substituted bis-indole derivatives and the metal complexes obtained therefrom constitute the active ingredients of pharmaceutical compositions which are useful, among others, in the diagnosis or therapy of ischemic diseases or space-occupying lesions in a patient, for instance for imaging a Ussue in a mammal, or as a necrosis-avid agent or as a multipurpose contrast agent for various organs or parts of organs of a mammalian body, wherein the multipurpose function includes at least one of a blood pool agent, a liver agent and a kidney agent. The present invention also relates to a method for generating an image of at least a part of the body of a mammal, comprising systemically or locally administering to the said mammal a contrast agent effective amount of such a metal-complexable substituted bis-indole derivative or a metal complex or a pharmaceutically acceptable salt thereof.

BRIEF DESCRIPTION OF THE DRAWINGS

FIG. 3E shows a photograph of a macroscopic histological slice corresponding to the same MRI image, obtained after sacrificing the same rat (arrows indicate necrotic liver lobe, S stands for stomach).

FIG. 4D shows a photograph of a heart section of the same pig.

FIG. 6F shows a photograph of a histological cross- section of the same rat.

DETAILED DESCRIPTION OF THE INVENTION

Figure 1:
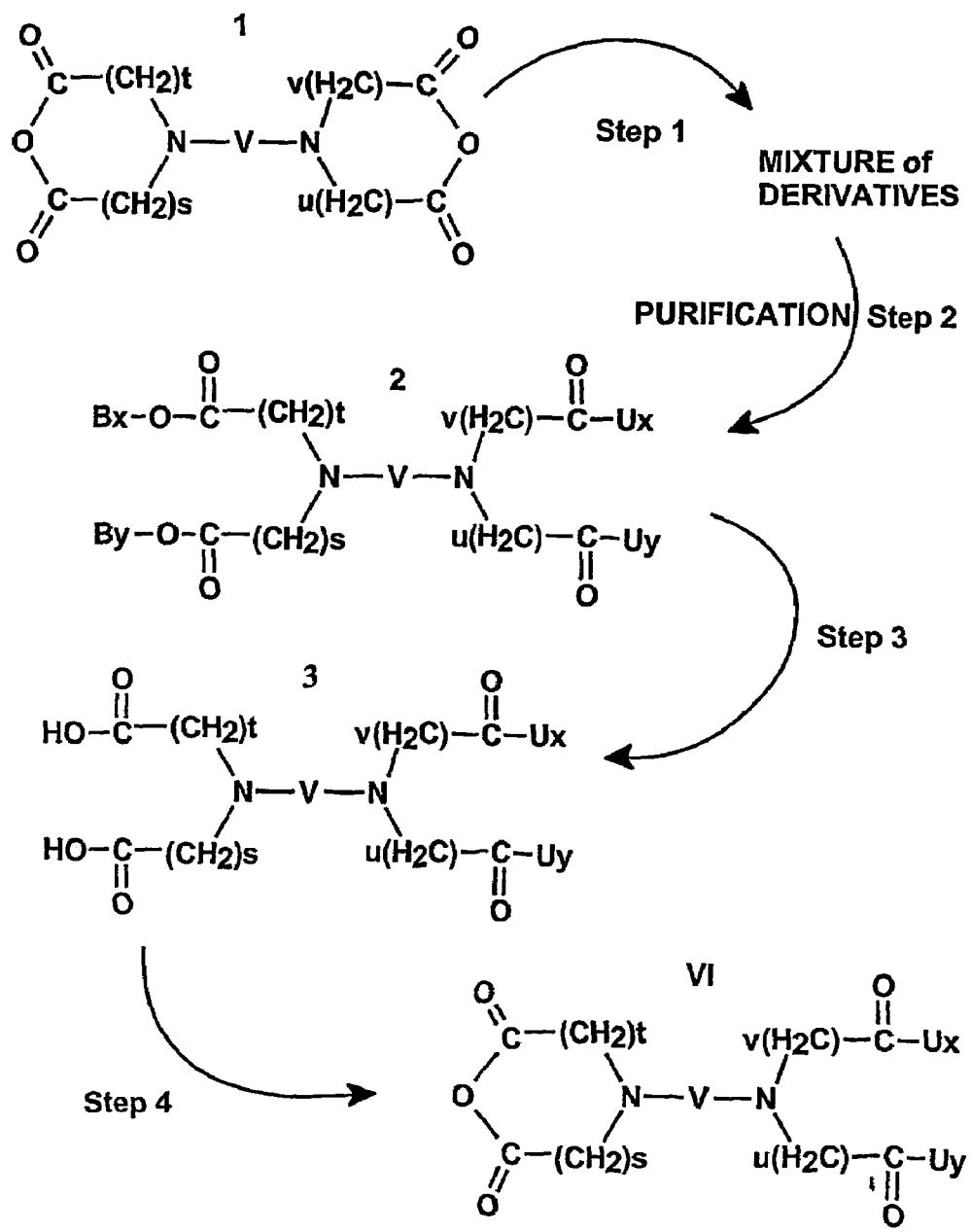
FIG. 1 schematically shows a synthesis procedure to obtain mono-reactive anhydride bifunctional chelating agents which are useful in preparing the metal-complexable bis-indole derivatives of the invention.
Figure 2:
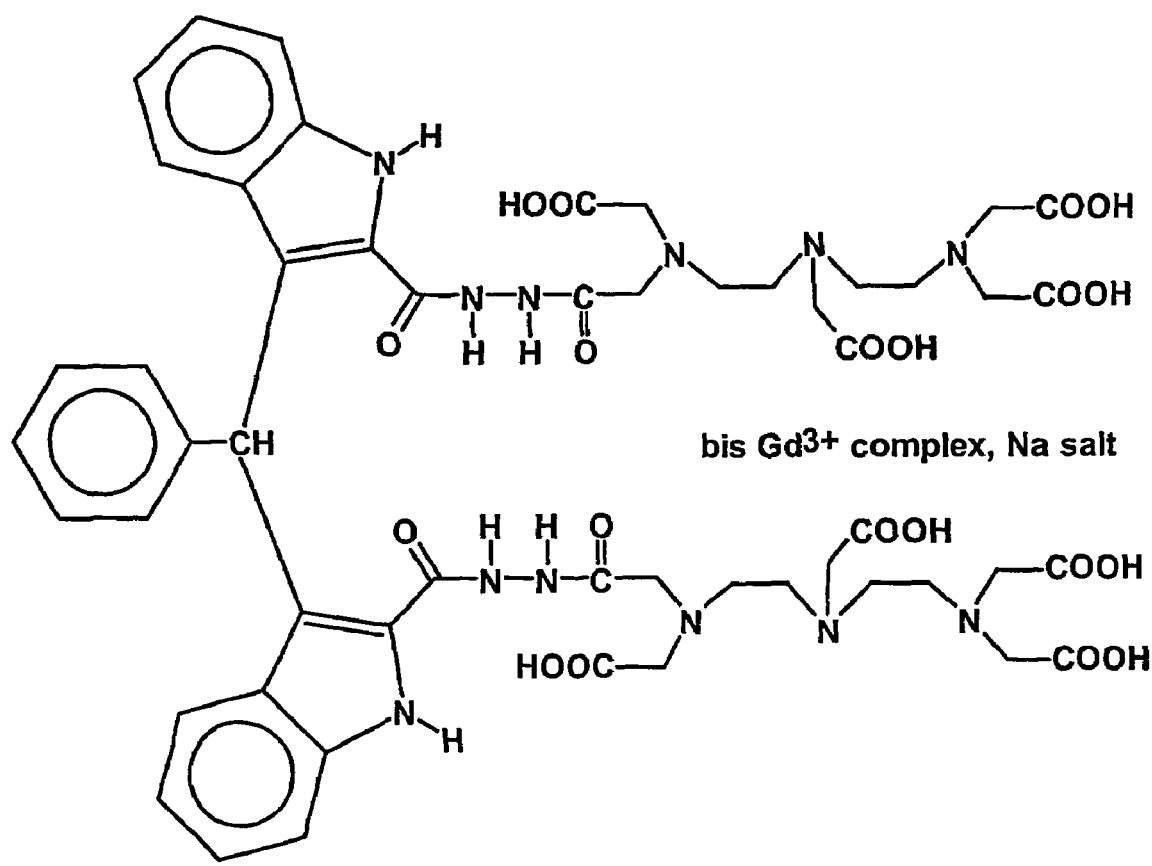
FIG. 2 shows the detailed formula of one exemplary metal-complexable bis-indole derivative according to the invention (the compound of example 8).

In accordance with a first aspect of the present invention, metal-complexable substituted bis-indole derivatives are provided comprising the structure shown in formula (I) hereunder:

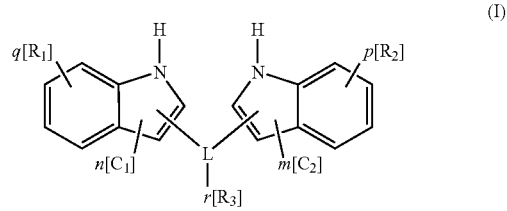

(I)

wherein:
L represents a single bond or an optionally substituted linking agent (Li) which covalently links together the carbon atoms being respectively in positions 2 or 3 and 2' or 3' on the heterocyclic rings of the indolyl groups;
$R_1$ and $R_2$ are optional substituents of any free position of the phenyl rings of the indolyl groups;
$R_3$ is an optional substituent of the linking agent (Li);
q, p and r are integers indicating the number of the respective substituents $R_1$, $R_2$ and $R_3$, provided that r is 0 when L is a single bond;

$C_1$ and $C_2$ are optional metal-complexing substituents of the heterocyclic rings of the indolyl groups;

m and n are integers indicating the number of the respective metal-complexing substituents $C_1$ and $C_2$ and are each 0 or 1, provided that the sum of m and n is at least 1.

Preferred embodiments of the metal-complexable substituted bis-indole derivatives of the present invention are those wherein at least one of the following limitations is met:

m is 1 and n is 1;

at least one of m and n is 1 and the metal-complexing substituent $C_1$ or $C_2$ is in an α position with respect to the single bond L or linking agent (Li);

m is 1, n is 1 and the metal-complexing substituents $C_1$ and $C_2$ are both in α positions with respect to the single bond L or linking agent (Li);

the linking agent (Li) is selected from the group consisting of a bridging at least divalent heteroatom, a disulfide bridge and an optionally substituted alkylene group wherein the alkylene chain may be interrupted by one or more heteroatoms; examples of suitable at least divalent heteroatoms include oxygen and sulfur; when sulfur is used as a heteroatom, (Li) may also be SO or $SO_2$; examples of suitable alkylene groups include methylene, ethylene and straight-chain or branched-chain alkylene groups having from 3 up to 6 carbon atoms (such as trimethylene, tetramethylene or hexamethylene), each hydrogen atom of the said alkylene groups being possibly substituted with an R3 substituent such as defined hereinbelow in more detail; when the alkylene chain is interrupted by one or more heteroatoms, the latter are preferably selected from oxygen and sulfur, more preferably oxygen, and the number of such heteroatoms is preferably up to 6, a specific example being a polyethoxy chain.

preferably the linking agent (Li) is a methylene group optionally substituted with one or two substituents $R_3$, the said substituents $R_3$ being preferably non-functional, i.e non reactive with chemical functions born by other parts of the bis-indole derivatives of the invention, in particular by the metal-complexing substituents thereof;

more preferably the linking agent (Li) is a methylene group substituted with one or two substituents $R_3$, each substituent $R_3$ being an optionally substituted aryl or heteroaryl group or an optionally substituted branched chain or straight chain alkyl group having from 1 to 20 carbon atoms, wherein the substituents on the said alkyl, aryl or heteroaryl group are preferably substituents which are not easily oxidable, such as halogen atoms (including fluorine, chlorine, bromine and iodine), saturated or unsaturated hydrocarbon groups having 1 to 4 carbon atoms (in particular alkyl groups such as methyl, ethyl, n-propyl, isopropyl, n-butyl, isobutyl and tert-butyl), alkoxy groups having 1 to 4 carbon atoms (including methoxy, ethoxy, propoxy and butoxy), cyano, carboxylic acid, sulfonic acid, carboxylic acid ester wherein the ester group derives from an alkyl group having 1 to 4 carbon atoms (such as above defined), substituted or unsubstituted carboxylic acid amides $CO-NR_4R'_4$ or substituted or unsubstituted amines $NR_4R'_4$ (wherein $R_4$ and $R'_4$ are each independently selected within radicals having the meaning indicated for $R_4$ under the heading of chelating agents hereinbelow); substituents on the aryl or heteroaryl group which should preferably be avoided are hydroxyl, mercapto and groups similarly susceptible of causing oxidation of the compounds of the invention and consequently susceptible of causing a significant discoloration of physiologically acceptable solutions containing the said compounds; suitable examples of the aryl group $R_3$ are phenyl, 4-biphenyl, 1-naphtyl, 2-naphtyl and 2-fluorenyl; suitable examples of the heteroaryl group $R_3$ are pyridinyl, quinolinyl, isoquinolinyl, thiophenyl, imidazolyl, pyrrolyl, furanyl, carbazolyl and $N$-$(C_1$-$C_4)$alkyl substituted carbazolyl; the number of substituents on the aryl or heteroaryl group $R_3$ may typically be from 0 to 3 or even more, depending on the number of carbon atoms of the said group;

each of p, q and r is independently selected from integers ranging from 0 to about 4.

Preferably, linking agents (Li) being a substituted methylene group may be derived from aliphatic, aromatic or heteroaromatic aldehydes such as (in the following non-exhaustive list, use of the plural is meant to include all possible isomers) benzaldehyde, mono- and polyhalogenated benzaldehydes, cyano-benzaldehydes, substituted or non-substituted aminobenzaldehydes, mono- and dinitro-benzaldehydes, mono- and polyalkoxybenzaldehydes, mono- and polyalkylated benzaldehydes, carboxylated benzaldehydes, aryloxy-benzaldehydes, 2-fluorenecarboxaldehyde, naphthaldehydes, alkoxy-naphthaldehydes, N-ethyl-3-carbazole-carboxaldehyde, 4-formylcinnamic acid, alkylthiobenzaldehydes, 2-formylbenzenesulfonic acid, methylformylbenzoate, acetaminobenzaldehyde, aryloxy-alkylbenzaldehydes, acetamidobenzaldehyde, alkylsulfonyl-benzaldehyde, propionaldehyde, butyraldehyde and so on.

Preferred $C_1$ and $C_2$ metal-complexing substituents are each independently represented by the formula $-(Sp)_s$-CA, wherein CA is a chelating agent, (Sp) is a spacing agent being attached (i.e. covalently linked) both to the heterocyclic ring of the indolyl group and to the chelating agent CA, and s is an integer selected from 0 and 1 (thus meaning that the spacing agent (Sp) is optional in the structure of the metal-complexable bis-indole derivative of the present invention). In particular, s may be 0 when an amino substituent is present on a heterocyclic ring of an indolyl group and the chelating agent CA comprises a terminal functional group, such as carboxylic acid, acid halide or acid ester that is able to readily react with the said amino substituent or when an amino substituent is present on the chelating agent CA and a heterocyclic ring of an indolyl group comprises a terminal functional group, such as carboxylic acid, acid halide or acid ester that is able to readily react with the said amino substituent. However, when introducing an amino substituent on the heterocyclic ring of an indolyl group proves to be difficult, then preferably s is equal to 1.

In the previous definition of $C_1$ and $C_2$, the structure of the chelating agent CA may comprise:

one or more thiol bearing moieties such as for example bisamine-bisthiol, bisamine-bisoxime, monomercapto-triamide, diamide-dithiol, monoamine-monoamide-dithiol, tetramine, monoamine-diamide-monothiol, monoamine-monothioether-dithiol, monoamine-monothiol, monoamine-diamine-monothiol and diphosphine based moieties (for reasons of stability of the complex formed with certain metals, this type of chelating agent is preferred namely when the metal is technetum-99m, rhenium-186 or rhenium-188); and/or one or more structural elements with the following formulae

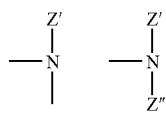

wherein Z' is a radical selected from the group consisting of phosphonomethyl (—$CH_2PO_3HR_4$), carboxymethyl (—$CH_2COOR_4$) and its derivatives (—$CHR_5COOR_4$), carboxyethyl (—$CH_2CH_2COOR_4$) and its derivatives (—$CHR_5CH_2COOR_4$ and —$CH_2CHR_5COOR_4$); Z" is hydrogen or a radical in the meaning of Z' or hydroxyethyl —$CH_2CH_2OH$ or its derivatives —$CHR_5CH_2OH$ and —$CH_2CHR_5OH$), i.e. for instance the nitrogen atom together with Z' and the optional Z" stand for iminoacetic acid, iminopropionic acid, iminodiacetic acid, iminodipropionic acid, iminoacetic propionic acid, hydroxyethyl iminoacetic acid and hydroxyethyl iminopropionic acid; $R_4$ is selected from hydrogen and optionally substituted $C_1$–$C_{20}$ branched chain or straight chain alkyl groups or $C_6$–$C_{20}$ aryl groups or $C_6$–$C_{20}$ alkylaryl groups, wherein the substituents on the alkyl, aryl or alkylaryl group may be for instance halogen atoms (including fluorine, chlorine, iodine and bromine), nitro, carboxy, amino, aminyl, amido or sulfono and wherein the number of such substituents may be from 0 to 3 or even more, depending on the number of carbon atoms of the said group; and $R_5$ is selected from groups in the meaning of $R_4$ or bonding groups comprising —CO— and/or —NH—, carboxy (—$COOR_4$), or radicals having the formula —$(CH_2)_{0-5}$—$(C_6H_4)_{0-1}$—$(O)_{0-1}$ —$(CH_2)_{0-1}$ —$(C_6H_4)_{0-1}$—$(O)_{0-1}$-M (II), or the formula —$(CH_2)_{0-5}$—$(C_6H_{10})_{0-1}$—$(O)_{0-1}$—$(CH_2)_{0-5}$—$(C_6H_4)_{0-1}$-M (III) wherein the integers appearing as subscripts of the hydrocarbylene or oxygen bonding groups indicate the minimum and maximum numbers of such groups and M is a group in the meaning of $R_4$, a —$CH_2CH_2COOR_4$ group, a bonding group comprising —CO— and/or —NH—, or a saturated, unsaturated or aromatic heterocyclic group comprising one or more heteroatoms (such as e.g. furfuryl and imidazolyl) and optionally substituted by up to 3 independent substituents being for instance such as listed hereinabove.

In accordance with the previous definitions, a first class of preferred chelating agents CA may be represented by one of the following formulae:

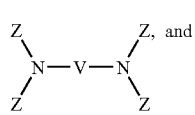

(IV)

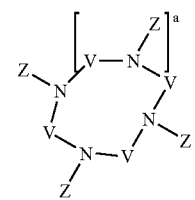

(V)

wherein a is an integer ranging from 0 to 6, each V independently represents an optionally substituted saturated, unsaturated or aromatic organylene group, such as phenylene, diphenylene, straight-chain or branched-chain hydrocarbylene group wherein the chain or part of it may form a cyclic or heterocyclic ring and wherein the hydrocarbylene group may also contain a phenylene, oxygen, sulfur, aminyl, N-substituted aminyl, carbonyl or thiocarbonyl group; the optional substituents of the said organylene group being preferably such as listed hereinabove with reference to the substituents of an aryl or heteroaryl group $R_3$ of the linking agent (Li) or being radicals having the formulae (II) or (III) hereinabove or being hydroxyl or mercapto groups, and each Z independently represents hydrogen or —$CHR_5$-Q or —CO—$CHR_5$-Q or —$CHR_5$—$CHR'_5$-Q, wherein Q is a bonding group selected from —CO—, —NH—, carboxy (—$COOR_4$), phosphono (—$PO_3HR_4$), amido (—$CONR_4R'_4$), hydroxy, alkoxy and aryloxy —$OR_4$, thiol, mercapto—$SR_4$, hydrazo (—CO—NH—$NHR_4$) and saturated, unsaturated or aromatic heterocyclic groups comprising one or more heteroatoms (such as e.g. furfuryl, pyridyl and imidazolyl) and optionally substituted by up to 3 independent substituents being preferably non-easily oxidable substituents such as listed hereinabove with reference to the substituents of a heteroaryl group $R_3$, and further wherein $R_4$ and $R_5$ are as defined- hereinabove and $R'_4$ and $R'_5$ have respectively the same meaning as $R_4$ and $R_5$.

Among the chelating agents CA of formula (IV) which comprise one or more thiol or mercapto groups, V is preferably —$CH_2$—$CH_2$—, —CO—$CH_2$—, —$(CH_2)_2$—NH—$(CH_2)_2$— or —$(CH_2)_2$—N(-Z)-$(CH_2)_2$—. In this case, preferred are chelating agents CA having one or more aminyl Z substituents independently selected from thioethyl and derivatives thereof (—$CH_2CH_2SR_4$), —$COCH_2SR_4$, thiomethyl and derivatives thereof (—$CH_2SR_4$), the remaining aminyl Z substituents being preferably selected from hydrogen, phosphonomethyl, carboxymethyl and derivatives thereof, carboxyethyl and derivatives thereof, hydroxyethyl and derivatives thereof such as previously defined (and including —$CH_2CH_2OR_4$). Additionally, one or more of the remaining aminyl Z substituents may represent a heterocyclic group such as previously indicated. Suitable examples thereof include the following:

derivatives of a mercaptoacetyl tripeptide such as mercaptoacetyl triglycine, an ethylene diamine dioxime tetraligand, a butylene diamine dioxime tetraligand or a propylene diamine dioxime tetraligand bearing one or more alkyl substituents (the said alkyl substituent being a group including from 1 to 8 carbon atoms) such as hexamethylpropylene diamine dioxime (HMPAO), ethylene dicysteine, ethylene cysteine cysteamine, cysteinylglycine cysteine, bismercaptoacetyldiaminopropionic acid, bismercaptoacetyidiaminosuccinic acid, bismercaptoacetyidiaminobutyric acid, N-(mercaptoacetylaminoethyl)cysteine, dimercaptosuccinic acid, dimercaptopropionic acid, cysteine, cysteamine, diphosphinopropionic acid, and derivatives thereof wherein one or more thiol functions are protected by a suitable $R_4$ group such as defined hereinabove.

The latter chelating agents are preferred namely when the complexing metal used is technetium-99m, rhenium-186 or rhenium-188.

Among the chelating agents CA of formulae (IV) and (V) hereinabove which do not comprise a thiol function, V is preferably —$CH_2$—$CH_2$—, —$(C_5H_8)$—, —$(C_6,H_{10})$—, —$(CH_2)_2$—NH—$(CH_2)_2$— or —$(CH_2)_2$—N(-Z)-$(CH_2)_2$—, and the integer a in formula (V) is preferably 0 or 1. In this case, preferred chelating agents have two or more, preferably three to five, aminyl Z substituents each independently selected from the group consisting of carboxymethyl (—CH$_2$COOR$_4$) and derivatives thereof (—CHR$_5$COOR$_4$), carboxyethyl (—CH$_2$CH$_2$COOR$_4$) and derivatives thereof (—CHR$_5$CHR'$_5$COOR$_4$). Remaining aminyl Z substituents are preferably each independently selected from hydrogen, phosphonomethyl, carboxymethyl and derivatives thereof, carboxyethyl and derivatives thereof, hydroxyethyl and derivatives thereof (such as previously defined), methylamido (—CH$_2$CO—NH$_2$) or derivatives thereof (—CH$_2$CO—NH—R$_4$ and —CH$_2$CO—NR$_4$R'$_4$), ethylamido (—CH$_2$CH$_2$CO—NH$_2$) or derivatives thereof (—CH$_2$CH$_2$CO—NHR$_4$ and —CH$_2$CH$_2$CO—NR$_4$R'$_4$), methylhydrazido (—CH$_2$CO—NH—NHR$_4$ and —CH$_2$CO—NH—NR$_4$R'$_4$), ethylhydrazido (—CH$_2$CH$_2$CO—NH—NHR$_4$ and —CH$_2$CH$_2$CO—NH—NR$_4$R'$_4$). Additionally, one or more of the remaining aminyl Z substituents can represent a straight-chain or branched-chain saturated or unsaturated alkyl group optionally substituted by halogen atoms and/or functional groups and optionally comprising a saturated, unsaturated or aromatic heterocyclic group comprising one or more heteroatoms and optionally bearing up to 3 independently selected substituents, such as for instance (furfuryl)alkyl, (hydroxyfurfuryl)alkyl, (imidazolyl)alkyl, (methylimidazolyl)alkyl, benzyl, benzyloxymethyl, 4-carboxymethoxybenzyl, 4-methoxybenzyl, 4-ethoxy-benzyl, 4-butoxybenzyl, 4-benzyloxybenzyl, 4-(4-methyloxybenzyloxy)-benzyl, methyl, propyl, isopropyl, n-butyl, sec-butyl, tert-butyl, pentyl, cyclopentyl, cyclohexyl, hydroxymethyl, 2-hydroxyethyl, 2-hydroxy-1-(hydroxymethyl)ethyl, 3-hydroxypropyl, 2-hydroxyisobutyl, 2,3-dihydroxypropyl, hydroxybutyl, 4-hydroxy-2-methylbutyl, 2,3,4-trihydroxybutyl and 2,3,4,5,6pentahydroxyhexyl.

Chelating agents CA of formulae (IV) and (V) which do not comprise a thiol function preferably have carboxymethyl groups (—CH$_2$COOR$_4$ wherein R$_4$ is as defined above) as the predominant aminyl Z substituents. Suitable examples thereof include:

ethylenediaminetetraacetic acid (usually referred as EDTA), diethylerie triaminopentaacetic acid (DTPA), trans-1,2-cyclohexanediamine tetraacetic acid (CDTA), 1,4,7,10-tetraazacyclododecane tetraacetic acid (DOTA), 1,4,7-triazacyclononanetriacetic acid, 1,4,8,11-tetraazacyclotetradecanetetra-acetic acid (TETA), ethyleneglycol-O,O'-bis(2-aminoethyl)tetraacetic acid (EGTA), N,N-bis(hydroxybenzyl)ethylenediamine-N,N'-diacetic acid (HBED), triethylenetetramine hexaacetic acid (TTHA), hydroxyethyldiamine triacetic acid (HEDTA) and 1,5,9-triazacyclo-dodecanetriacetic acid, and analogues of the above compounds wherein one or more carboxymethyl groups are replaced by hydrogen and/or by another aminyl Z substituent in such a way that Z together with the aminyl group to which it is attached comprises one of the following: aminoethanol, 2-amino-2-ethyl-1,3-propanediol, 3-methyl-1-butamine 6-amino-2-methyl-2-heptanol, 2-(2-aminoethoxy)ethanol, 1-(3-aminopropyl) imidazole, 4-(3-aminopropyl)morpholine, 1-(3-aminopropyl)-2-pipecoline, 1-(3-aminopropyl)-2-pyrrolidinone, 1-(2-aminoethyl)pyrrolidine, 1-(2-aminoethyl)piperidine, 2-(2-aminoethyl)pyridine, 2-(aminomethyl)pyridine, 1-(2-aminoethyl)pyrrolidine, 4-(2-aminoethyl)morpholine, 4-(2-aminoethyl)-1-methylpyrrolidine, (aminomethyl)cyclopropane, 2-(aminomethyl)pyridine, 3-(aminomethyl)pyridine, 2-(aminomethyl)-1-ethylpyrrolidine, furfurylamine, tetrahydrofurfurylamine, 2-(aminomethyl)-tetrahydropyran, 2-(aminomethyl)-1,3-dioxolane, 2-(aminomethyl)-1-methylimidazole, N-(2-aminoethyl) piperidine, N-(2-aminoethyl)morpholine, 3-(2-aminoethyl)indole, naturally occurring amino-acids such as glycine (equivalent to a carboxymethyl Z substituent), leucine, isoleucine, isoleucinol, alanine, β-alanine, valine, tyrosine, serine or threonine, and analogues thereof such as their carboxamide, hydrazide or ester. Suitable examples of such analogues include N-(2-hydroxyethyl) diethylenetriamine N,N',N'',N''' tetraacetic acid and N-(2-hydroxyethyl) ethylenediamine N,N',N'' triacetic acid.

Among the chelating agents CA of formulae (IV) and (V), especially preferred are those having structures represented by any of the following formulae 10a–10g and 11a–11b:

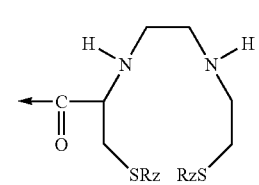

Formula 10a

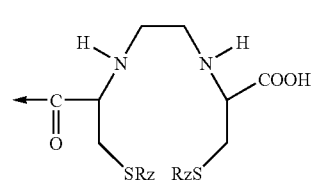

Formula 10b

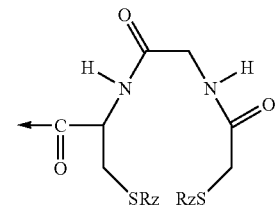

Formula 10c

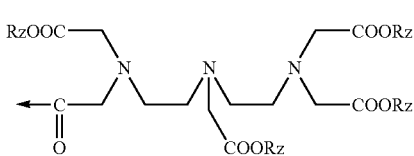

Formula 10d

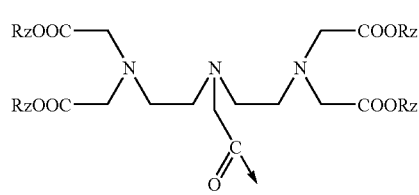

Formula 10e

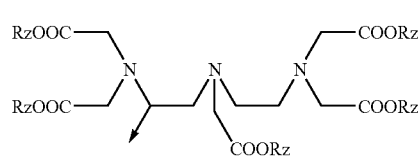

Formula 10f

-continued

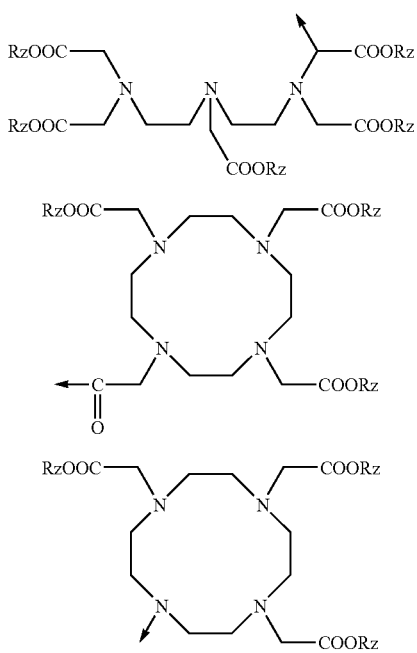

Formula 10g

Formula 11a

Formula 11b wherein the arrow indicates the bonding position of the said chelating agent to the ring system A and/or B or to the optional spacing agent (Sp), and wherein $R_Z$ has the same meaning as described for the radical $R_4$ hereinabove.

Other classes of alternatively suitable chelating agents CA which may be used in the present invention have been extensively described in the prior art, for instance in U.S. Pat. Nos. 6,221,334, 6,056,939, 5,556,939, 5,527,885, 5,326,856, 5,220,000, 5,202,451, 5,196,515, 5,164,176, 5,585,468, 4,861,869, 5,436,352, 6,184,361, 5,808,003, 5,756,825 and 5,632,969, the content of which is incorporated herein by reference.

The optional spacing agent (Sp) which may be present in the metal-complexing substituents $C_1$ and/or $C_2$ is preferably a radical represented by the formula —X)$_t$-(Sp')-, wherein t is 0 or 1, (Sp') is derived from a molecule bearing:
at one end a first functional group (i), such as an amine, suitable for reacting with a carboxylic acid function (e.g. acid, acid halide or acid ester), for instance with the carboxylic acid function preferably present on the heterocyclic rings of the indolyl groups of a suitable 2,3-disubstituted bis-indole precursor compound bearing at least one carboxylic acid (halide or ester) or amino substituent; and
at the other end a second functional group (ii) suitable for reacting with the chelating agent CA of interest, and X is a carboxy group or a primary or secondary amino group.

Based on the above definition, the person skilled in the art is readily able to determine one or more suitable spacing agents (Sp) once the chelating agent CA has been selected. In practice, preferred spacing agents (Sp) are radicals derived from bis-amines, such as preferably hydrazine, or from amino-acids, such as detailed hereinafter in the context of the methods for producing the novel compounds of the invention.

The optional substituents $R_1$ and/or $R_2$ which may be present on the phenyl ring of the indolyl groups may be each independently selected for instance from the following list:
halogen atoms such as fluoro, chloro, iodo and bromo,
straight chain alkyl groups of 1 to 6 carbon atoms such as methyl, ethyl, n-propyl, n-butyl, n-pentyl and n-hexyl,
branched chain alkyl groups of 3 to 8 carbon atoms such as isopropyl, isobutyl, tert-butyl, isoamyl, methylpentyl, 2-ethylhexyl and the like,
cycloalkyl groups of 3 to 7 carbon atoms, in particular cyclopentyl and cyclohexyl,
straight chain and branched chain alkoxy groups of 1 to 6 carbon atoms such as methoxy, ethoxy, propyloxy, buyloxy and amyloxy,
trifluoromethyl,
cyano,
carboxylic acid,
sulfonic acid,
carboxylic acid ester (wherein the ester group derives from an alkyl group having 1 to 4 carbon atoms (such as above defined), and
substituted or unsubstituted amines $NR_4R'_4$ (wherein $R_4$ and $R'_4$ have the meaning indicated hereinbefore).

Of particular importance here is the fact that, alike for the optional substituents of an aryl or heteroaryl group $R_3$, the $R_1$ and/or $R_2$ substituents are preferably substituents which are not easily oxidable. Therefore, hydroxyl and mercapto groups and other functional groups similarly susceptible of causing oxidation of the compounds of the invention and consequently susceptible of causing a significant discoloration of physiologically acceptable solutions containing the said compounds should preferably be avoided.

As previously set forth, the single bond or linking agent L covalently links together the carbon atoms being respectively in positions 2 or 3 and 2' or 3' (using conventional nomenclature rules) on the heterocyclic rings of the indolyl groups of the bis-indole derivatives of the invention. This means that within the broad chemical structure shown in formula (I), three distinct sub-families of derivatives may be recognized as follows:
a sub-family wherein L covalently links the carbon atoms being respectively in positions 3 and 3', having the structure shown in formula (Ia) hereunder:

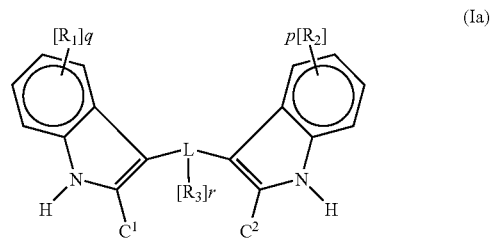

(Ia)

wherein L, $C_1$, $C_2$, $R_1$, $R_2$, $R_3$, p, q and r are as defined hereinabove,
a sub-family wherein L covalently links the carbon atoms being respectively in positions 2 and 2', having the structure shown in formula (Ib) hereunder:

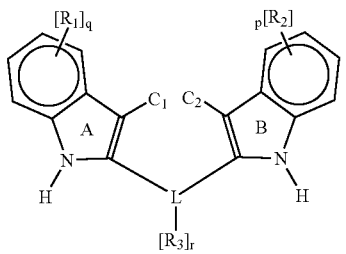

(Ib)

wherein L, $C_1$, $C_2$, $R_1$, $R_2$, $R_3$, p, q and r are as defined hereinabove, and A and B designate the heterocyclic rings of the indolyl groups, and a sub-family wherein L covalently links the carbon atoms being respectively in positions 2 and 3'.

Exemplary useful and readily available metal-complexable substituted bis-indole derivatives corresponding to formula (Ia) are for instance selected from the group consisting of:

[{2-[N'-(3-{[2-(N'-{2-[(2-{[2-bis(carboxymethylamino)-ethyl]carboxymethyl-amino}ethyl)carboxymethylamino]-acetyl}hydrazinocarbonyl)-1H-indol-3-yl]-phenyl-methyl}-1H-indole-2-carbonyl)-hydrazino]-2-oxo-ethyl}-(2-{[2-bis(carboxymethyl-amino)-ethyl]-carboxymethylamino}-ethyl)-amino]-acetic acid,

[{2-[N'-(3-{[2-(N'-{2-[(2-{[2-bis(carboxymethyl-amino)-ethyl]carboxymethyl-amino}-ethyl)carboxymethyl-amino]-acetyl}-hydrazinocarbonyl)-1H-indol-3-yl]-methyl}-1H-indole-2-carbonyl)-hydrazino]-2-oxo-ethyl}-(2-{[2-bis(carboxymethyl-amino)-ethyl]-carboxymethylamino}-ethyl)-amino]-acetic acid, {4,7-bis-carboxymethyl-10-[({3-[(2-{N'-[(4,7,10-tris-carboxymethyl-1,4,7,10-tetraaza-cyclododec-1-yl)-acetyl]-hydrazinocarbonyl}-1H-indol-3-yl)-methyl]-1H-indole-2-carbonyl}-hydrazino)-2-oxo-ethyl]-1,4,7,10-tetraaza-cyclododec-1-yl]-acetic acid, {4,8-bis-carboxymethyl-11-[({3-[(2-{N'-[(4,8,11-tris-carboxymethyl-1,4,8,11-tetraaza-cyclotetradec-1-yl)-acetyl]-hydrazinocarbonyl}-1H-indol-3-yl)-methyl]-1H-indole-2-carbonyl}-hydrazino)-2-oxo-ethyl]-1,4,8,11-tetraaza-cyclotetradec-1-yl)acetic acid, enantiomers and pharmaceutically acceptable salts (including alkaline salts and ammonium salts) thereof.

Such salts include sodium and potassium salts and tertiary ammonium salts $NR_4R'_4R''_4R'''_4$ (wherein $R_4$, $R'_4$, $R''_4$ and $R'''_4$ are each independently selected within the meaning of $R_4$ provided hereinabove under the heading of radicals Z' of the chelating agents). More particularly useful are the sodium salts of:

[{2-[N'-(3-{[2-(N'-{2-[(2-{[2-bis(carboxymethyl-amino)-ethyl]carboxymethylamino}-ethyl)carboxymethyl-amino]-acetyl}-hydrazinocarbonyl)-1H-indol-3-yl]-phenyl-methyl}-1H-indole-2-carbonyl)-hydrazino]-2-oxo-ethyl}-(2-{[2-bis(carboxymethyl-amino)-ethyl]-carboxymethylamino}-ethyl)-amino]-acetic acid, and

[{2-[N'-(3-{[2-(N'-{2-[(2-{[2-bis(carboxymethyl-amino)-ethyl]carboxymethylamino}-ethyl)carboxymethyl-amino]-acetyl}-hydrazinocarbonyl)-1H-indol-3-yl]-methyl}-1H-indole-2-carbonyl)-hydrazino]-2-oxo-ethyl}-(2-{[2-bis(carboxymethyl-amino)-ethyl]-carboxymethylamino}-ethyl)-amino]-acetic acid.

The term "enantiomers", as used herein, means each individual optically active form of the compound of the invention, having an optical purity (as determined by methods standard in the art) of at least 80%, preferably at least 90% and more preferably at least 98%.

In the following part of the description, it should be understood that, although alternative chemical routes may exist, a suitable and preferred method for preparing the metal-complexable substituted bis-indole derivatives corresponding to formula (I) involves the following steps:

(a) a bis-indole compound, wherein the carbon atoms being respectively in positions 3 and 3' or 3 and 2' or 2 and 2' on the heterocyclic rings of the indolyl groups are covalently linked through L, i.e. through a single bond or an optionally substituted linking agent (Li), the said bis-indole compound optionally comprising one or two reactive groups in α-position with respect to L, is first prepared by a coupling reaction involving (i) one mono-indole or two different mono-indoles each optionally comprising one reactive group, the said reactive group being preferably a carboxylic group (for instance a carboxylic acid, a carboxylic acid halide or a carboxylic alkyl ester group) or an amine, and (ii) an aldehyde comprising the moiety (Li), (b) at least one reactive group, if not already present on the bis-indole compound from step (a), is introduced onto the heterocydic ring of at least one indolyl group of the said bis-indole compound, in α-position with respect to L, the said reactive group being preferably a carboxylic group (for instance a carboxylic acid, a carboxylic acid halide or a carboxylic alkyl ester grou) or an amine, (c) the reactive group(s) mentioned in step (a) or step (b) is (are) optionally reacted, usually by a coupling reaction, with at least one spacing agent Sp such as previously defined (i.e. bearing at least two functional end groups) and (d) the second functional end group of the spacing agent Sp is reacted, usually by a coupling reaction, with a suitable chelating agent CA, such as previously defined, or a chelating agent precursor being able to introduce the desired chelating moiety into the metal-complexable derivative of the invention.

Whilst the mono-indoles and the coupling reaction conditions of step (a) are well known in the art, the same cannot be said of the 2,3-disubstituted bis-indole intermediates or precursor compounds obtained after step (b) and/or after step (c), which are novel chemical compounds having utility in the preparation of the metal-complexable derivatives of the invention.

Therefore, in accordance with a second aspect of the invention, a first class of novel precursor compounds for the metal-complexable substituted bis-indole derivatives of formula (I) consists of compounds obtained after step (c), being 2,3-disubstituted bis-indole compounds optionally having one or more spacing agents (Sp) attached, in α-position which with respect to L, to the heterocyclic ring(s) of the indolyl group(s).

Specific examples of this first class of novel precursor compounds are the bis-hydrazides (3'-{[(2-hydrazinocarbonyl)-1H-indol-3-yl]-phenyl-methyl-1H-indole-2-carbonyl)-hydrazine and (3'-{[(2-hydrazinocarbonyl)-1H-indol-3-yl]-methyl}-1H-indole-2-carbonyly)-hydrazine, their indol-2-yl isomers (i.e., using trivial names, 3,3'-benzylidenebis(indole-2-carboxylic acid hydrazide) and 3,3'-methylenebis(indole-2-carboxylic acid hydrazide) and analogues thereof. The term "analogues" makes reference to similar compounds wherein (i) the phenyl ring of each indolyl group may be independently substituted with substituents $R_1$ and/or $R_2$ such as previously defined for the derivatives of formula (I) and/or wherein (ii) the methylene or benzylidene bridging group between the indolyl groups may be replaced with a single bond or with any other linking agent (Li) such as previously defined for the derivatives of formula (I) and/or wherein (iii) hydrazine is replaced by another bis-amino or amino-acid radical, as defined hereinafter.

Altogether, this first class of novel precursor compounds comprise the structure shown in formula (VIII) hereunder:

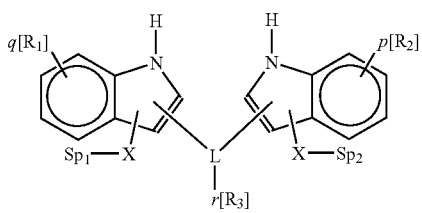

wherein:

$L$, $R_1$, $R_2$, $R_3$, p, q and r are as defined hereinabove, and

X and each of $Sp_1$ and $Sp_2$ respectively have the meaning of X and Sp' given hereinabove.

This first class of precursor compounds may be readily prepared during step (c) by reacting a spacing agent—such as hydrazine, a bis-amine or an amino-acid—with a bis-indole compound comprising at least one group reactive with the first functional end group of the said spacing agent Sp, for instance a 2,3-disubstituted carboxylated bis-indole such as 3'-{[(2-alkyloxycarbonyl)-1H-indol-3-yl]-phenyl-methyl}-1H-indole-2-carboxylic acid ethyl ester, their indol-2-yl isomers and analogues thereof wherein (i) the phenyl ring of each indolyl group may be independently substituted with substituents $R_1$ and/or $R_2$ such as previously defined and/or wherein (ii) the methylene or benzylidene bridging group between the indolyl groups may be replaced with a single bond or with any other linking agent (Li) such as previously defined. The latter may be referred as a second class of novel precursor compounds, being intermediates useful for the preparation of the precursors of the first class. These 2,3-disubstituted carboxylated bis-indoles in turn can be suitably prepared either according to step (b) or by another procedure comprising coupling one or more mono-indole compounds, at least one of them bearing a carboxylic group-containing substituent (for instance a carboxylic acid, a carboxylic acid halide or a carboxylic alkyl ester group) or an amino-containing substituent (for instance an alkylene amine —$(CH_2)_n$—$NH_2$,) in $\alpha$-position or $\beta$-position (depending whether a compound of formula (Ia) or a compound of formula (Ib) is desired in the final step) with respect to the nitrogen atom of the indolyl group, by means of a known coupling agent. Suitable coupling agents for this purpose include aromatic and heteroaromatic aldehydes (an extensive list of which has been provided hereinbefore) or formaldehyde, thus yielding homodimeric or heterodimeric (i.e. symmetric or not) bis-indole carboxylic acid or bis-indole amino compounds, depending on whether one or two different mono-indole compounds were used in the said coupling reaction.

The second class of precursor compounds comprise the structure shown in formula (IX) hereunder:

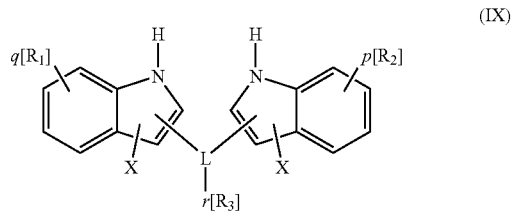

wherein L, $R_1$, $R_2$, $R_3$, p, q, X and r are as defined hereinabove.

A spacing agent (Sp) can be introduced into the bis-indole molecule during step (c) in various ways. These include for example the modification of one or more available W substituents as shown in formula (VII) hereinafter or the introduction of one or more new W substituents and/or combinations thereof. Again, use can be made of compounds referred to as homobifunctional spacing agent precursors (optionally with one or more function(s) in a protected form) or their heterobifunctional analogues in an optionally protected form. For instance, an $\alpha$-C(=O)—NH—$NH_2$ substituent can be derived by coupling an $\alpha$-carboxyl group with tert-butyl carbazate and a catalytic amount of a condensing agent such as dicyclohexylcarbodiimide, N-ethoxycarbonyl-2-ethoxy-1,2-dihydroxyquinoline, N,N'-carbonyldiimidazole, 2-isobutoxy-1-isobutoxy-carbonyl-1,2dihydroquinoline or the like, followed by deprotection in order to make the hydrazide available for further reaction. The same substituent can also be obtained by hydrazinolysis of a $\alpha$-carboxyl alkyl ester group with hydrazine. Hydrazinolysis, aminolysis and the like are appropiate alternative well known procedures for reactions involving condensing agents and precursors bearing protected functional groups which necessitate deprotection.

Analogues of the bis-hydrazide precursors of the first class are compounds for the preparation of which hydrazine is replaced with:

a bis-amine for instance selected from alkyl diamines having the formula $NH_2$—$(CH_2)_{2-12}$—$NH_2$ including 1,2-diaminoethane, 1,5-diaminopentane 1,6-diaminohexane, 1,7-diaminoheptane 1,2-diaminododecane and the like, alkyl diamines comprising one or more hetero atoms such as for example 1,8-diamino-3,6-dioxaoctane, 1,5-diamino-3-oxapentane; alkyl diamines comprising one or more optionally protected functional groups such as for example lysine and lysine; cyclic bis-amines such as for example piperazine and derivatives thereof; or an amino-acid, whether naturally-occurring or not, including a straight chain or branched chain hydrocarbon group with 1 to 6 carbon atoms.

Once a precursor compound of the first class is available, then a chelating agent CA can be introduced during step (d) of the preparation process, either directly or indirectly by making use of a precursor CA compound. As used herein, precursor CA compounds include but are not restricted to the well-known bi-functional chelating agents which, beside the functional groups (most often shielded by protective groups) necessary for metal complexation, bear a functional group (most often in an activated form, e.g. carboxylic acid esters comprising an appropriate leaving group) that can be specifically used in conjugation reactions. Accordingly, a bifunctional chelating agent is useful for introducing one or more CA functions into the bis-indole molecule. This can be accomplished by conjugating the bi-functional chelating agent directly to an atom which is part of the indolyl groups or the spacing agent (Sp), for example the nitrogen atom of a primary or secondary amine.

When step (d) involves an amine on the precursor compound of the first class (i.e. a bis-indole/spacing agent conjugate) or in case the bis-indole contains one or two amino-containing substituents on the heterocyclic rings of the bis-indoles, then a carboxylic acid group (or its activated form) of the chelating agent CA is usually involved in the coupling procedure, as is the case for instance in bi-functional chelating agents bearing an intra-molecular anhydride such as those derived from an iminodiacetic acid molecule portion (—N(CH$_2$COOH)$_2$), Exemplary compounds of this kind comprise the bis-anhydrides of EDTA, DTPA and the like (such as disclosed in French Patent No. 1.548.888) as well as the DTPA monoanhydride mono-ethyl ester. The latter compound may suitably be prepared from DTPA monoethyl ester by reacting with acetic anhydride in the presence of pyridine. Other bi-functional DTPA derivatives are known from the literature (see e.g. *J. Org. Chem.* (1990) 55:2868 and U.S. Pat. No. 5,514,810).

When step (d) involves an amine on the chelating agent CA, then one or two carboxylic acid groups (or their activated form) of the precursor compound of the first class (i.e. a bis-indole/spacing agent conjugate) may be involved in the coupling procedure.

For the preparation of DTPA monoethyl ester and related compounds, reference is now made to FIG. 1. The present invention includes a novel method for obtaining monoreactive mono-anhydrides comprising the structural formula VI in FIG. 1 via an intermediate which facilitates their purification. Such intermediate may be a monobenzyl ester obtained by reacting the corresponding bis-anhydride having the formula 1 shown at top of FIG. 1 with benzyl alcohol in the presence of a suitable reagent such as for example water, ammonia, primary or secondary amines, hydrazides or alcohols, such as detailed hereinafter.

In the formulae 1 and VI of FIG. 1:
the indicia s, t, u and v are each independently selected integers from 1 to 3, provided that the sum of s and t is not above 4 and that the sum of u and v is not above 4;
V is an organylene group such as described in detail in respect of formulae (IV) and (V) hereinabove; and
substituents U$_x$ and U$_y$ are freely but mutually exclusively selected from either the group comprising —OH and —O$^-$Cat$^+$, wherein Cat$^+$ is an organic cation, e.g. a carboxylic acid ammonium, sodium, calcium or potassium salt, or the group comprising aminyl radicals of formula —NH$_2$ or substituted derivatives thereof and ether-type radicals, i.e. U$_x$ and U$_y$ together with the neighbouring carbonyl group may be a carboxylic acid, a carboxylic acid salt, an (optionally N,N- or N-substituted) amide, a hydrazide or a bis acylhydrazide group.

The bis-anhydride analogue of formula 1 in FIG. 1, obtained for instance according to the method of French Patent No. 1,548,888, is dissolved (with optional heating) in a suitable anhydrous solvent (for example dimethylformamide) in the presence of a base which does not react with anhydrides (for example a tertiary amine such as triethylamine). Next, equimolar amounts of an alcohol preferably comprising one or more aromatic groups (for example benzyl alcohol) and a suitable reagent are added. When a maximal number of carboxylic groups is desired, then the said reagent is preferably a lower alcohol (such as for example methyl or ethyl alcohol) which can easily be removed by hydrolysis. When, on the other hand, a transformed carboxylic moiety is desired, then the reagent is preferably selected from amino, hydrazo and hydrazido compounds. Even when reaction conditions are optimal with respect to temperature, dilution and method of introduction of reactants, a substantial amount of by-products will be present. Hence, a second step involves the physical separation of the major reaction products. Selecting an alcohol comprising one or more aromatic groups in the first step enables purification to proceed under milder conditions, i.e. for example non-hydrolytic conditions with respect to lower alkyl esters) by using methods that allow separation based on differences in hydrophobicity and type of hydrophobic interaction. These methods typically include extraction-based procedures, chromatographic procedures using reversed phase chromatography on alkylated solid supports, adsorption chromatography on polymeric supports, and so on. Fractions containing the essentially pure compound of formula 2 in FIG. 1, wherein the B substituents mutually exclusively represent either a proton or the non hydroxyl portion of the alcohol used as the reagent of the previous step, are further processed by selective removal of the B substituents in step 3 in order to afford a compound (having formula 2 in FIG. 1) comprising a shielded terminal imino bis alkylcarboxylic acid group and an unprotected counterpart which, in final step 4 is converted into the desired monoreactive monoanhydride of formula VI.

For some applications (e.g. preparation of compounds comprising alkaline and/or acidic labile groups) it may be beneficial to accomplish coupling with DTPA comprising unprotected carboxyl group(s) (e.g. devoided of ester groups) because removing protective groups often necessitates stringent conditions (such as alkaline hydrolysis of the ester functions), as shown in one of the following examples.

To summarize, a chelating agent function CA can be introduced into a precursor compound of a bis-indole derivative of formula (I) at any stage of the synthesis. In particular, it may be introduced previously to condensing the indolyl groups, although it is more often advantageous and easier to introduce it at a later stage, as explained hereinabove. Exemplary novel precursor compounds according to the invention comprise the structure shown in formula (VII) hereunder:

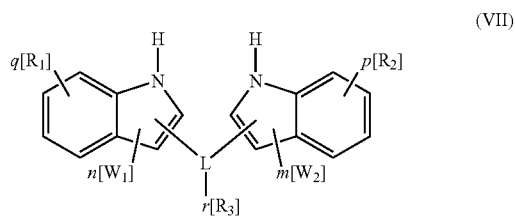

(VII)

wherein:
L, m, n, p, q and r are all as defined in formula (I) hereinabove, and
W$_1$ and W$_2$ are optional substituents which, optionally after adequate chemical modification, enable the attachment of metal-complexing substituents such as C$_1$ and C$_2$ of formula (I) respectively, and being at position 2 or 2' (when L is at position 3 or 3') or at position 3 or 3' (when L is at position 2 or 2') of each indolyl group, i.e. in α position with respect to L.

The precursor compounds of formula (VII) are preferably symmetric with regard to the indolyl groups, however due to the occurrence of possibly different substituents on the phenyl ring of the indolyl groups, and possibly due to the linking agent (Li), they may also be asymmetric.

After reaction with suitable metal-complexing substituents (i.e. chelating agents optionally separated from the indolyl group by a spacing agent), including optional chemical modification of the $W_1$ and/or $W_2$ substituents, substituted bis-indole derivatives having the structure shown in formula (I) are obtained from the first class of novel precursor compounds of this invention. For this purpose, a (second class) precursor compound bearing a carboxylic ester function (such as e.g. a 3'-{[(2-alkyloxycarbonyl)-1H-indol-3-yl]-phenyl-methyl}-1H-indole-2-carboxylic acid ester) can be converted via aminolysis (e.g. by means of ethylenediamine, piperazine, 2-methylpiperazine or other suitable diamines, including those cited above under the heading homobifunctional agents) or hydrazinolyis into an intermediate which readily reacts with a chelating agent precursor, e.g. with an anhydride (including DTPA monoethyl ester monoanhydride) or with any kind of in situ activated or mono-reactive bifunctional chelating agent. Accordingly chelating groups CA, including those cited in formulae 10a to 10g, 11a and 11b hereinabove, can be easily introduced into the final bis-indole derivative having the structure of formula (I).

According to the above-mentioned procedures, a multitude of specific substituted bis-indole derivatives, each embodying the structure of formula (I), may be produced which may exhibit some quantitative differences with respect to their properties in medical applications, such as blood clearance (ranging from relatively fast to relatively slow), elimination from the body (predominantly by kidney or shifted to hepatobiliary secretion), plasma protein binding (from low to high), etc. Labeling/complexation of the substituted bis-indole derivatives according to formula (I) can be accomplished, using methods well known in the art, by chelation with radioactive or non-radioactive metal ions, preferably with ions of an element with an atomic number selected from 21 to 32, 37 to 39, 42 to 44, 49, 50 or 57 to 83 such as for example:

Mn, Fe or Gd (with respect to non-radioactive metals), and $^{99m}$Tc, $^{111}$In, $^{67}$Ga, $^{90}$Y, $^{188}$Re, $^{186}$Re and $^{163}$Dy (with respect to radioactive metals).

Chelation with metal ions can be performed by methods well documented in the literature, i.e. at any stage of the production, although most often in the final step. When protected functional groups are present in the metal-complexing substituents, they may be partly or completely deprotected prior to metal chelation. Ionizable groups not involved in metal complexation may be optionally neutralized by acidic or basic counter-ions or by (inorganic and/or organic) compounds bearing ionizable acidic and/or basic groups. Remaining acidic protons, i.e. those that have not been substituted by the metal ion, can optionally be completely or partially replaced by cations of inorganic or organic bases, basic amino-acids or amino-acid amides. Suitable inorganic counter ions are for example the ammonium ion, the potassium ion, the calcium ion, the magnesium ion and, more preferably, the sodium ion. Suitable cations of organic bases are, among others, those of primary, secondary or tertiary amines, such as, for example, ethanolamine, diethanolamine, morpholine, glucamine, N,N-dimethylglucamine, tris(hydroxymethyl)aminomethane and especially N-methylglucamine. Suitable cations of amino-acids are, for example, those of lysine, arginine and omithine as well as the amides of any other acidic or neutral amino-acid such as for example lysine methylamide, glycine ethylamide or serine methylamide.

According to a third aspect of the present invention, the above-described substituted bis-indole derivatives of formula (I) and their metal complexes may be used in vitro, in vivo and/or ex vivo, for instance in the form of their pharmaceutically acceptable salts and/or in the form of pharmaceutical compositions comprising them in admixture with at least one pharmaceutically acceptable carrier, as diagnostic agents and/or therapeutic agents. For instance, these active ingredients are useful for the manufacture of medicaments suitable for imaging or imaging-aided applications, including magnetic resonance imaging (MRI), nuclear scintigraphy (NS), MRI-aided applications or NS-aided applications or for the manufacture of imaging agents or imaging-aided agents for use in such applications. This includes their use as in vivo effective contrast agents, including multipurpose contrast agents, for visualizing and/or identifying organs, parts of organs or systems such as for example the vasculatory system, the hepatobiliary system or the renal-urinary system, tissues such as for example necrotic tissue, and for visualizing and/or identifying diseases and pathologies. Diseases involved in this aspect of the invention include ischemic insults such as myocardial or cerebral infarction and space-occupying lesions (e.g. tumors or inflammatory lesions) in solid organs such as the liver, kidney, spleen, adrenal gland, etc. These agents are also useful in the follow-up of a therapy, for instance the evolution of necrosis. In particular, these contrast agents are useful in medical applications involving necrosis and necrosis-related pathologies, such as pathological or therapeutic necrosis caused by pathologic or therapeutically-induced ischemia or originating from trauma, radiation and/or chemicals, including therapeutic ablation, radiotherapy and/or chemotheraphy, myocardial and cerebral infarctions. For this purpose, they are administered to the human body, preferably enterally or parenterally, as therapheutic and/or diagnostic agents.

Pharmaceutically acceptable carriers for use in admixture with the biologically-active ingredients of this invention are well known in the art of pharmacy and will be selected depending on the mode of administration to the patient (i.e. the mammal, in particular humans) involved. Most often, a suitable formulation is a physiologically acceptable liquid formulation, preferably an aqueous solution or an emulsion or suspension including conventional surfactants such as polyethylene glycol.

In an another embodiment, the invention relates to a method for generating an image of at least a part of a body of a mammal, comprising systemically or locally administering to the mammal a contrast agent effective amount of a metal-complexable substituted bis-indole derivative or a metal complex thereof having the formula (I). Preferably, the contrast agents of the invention are used systemically as diagnostic agents by parenteral administration, including intravenous injection, at low doses, i.e. when a complexing metal such as gadolinium is used, i.e. at doses from about 10 to about 500 μmoles gadolinium per kg body weight, preferably at doses ranging from about 10 to about 50 μmoles gadolinium per kg body weight, the lower part of such ranges being still in vivo effective in case of systemic applications.

Alternatively, the contrast agents of the invention are also useful for local administration, e.g. including intracoronary administration in the case of a patient with myocardial infarction. Depending on the specific case, an effective local dose of the contrast agent of the invention may be from 1 to about 5 μmoles gadolinium per kg body weight of the patient to be treated.

Yet alternatively, when a radioactive complexing metal such as indium-111 is used, the metal complex may be administered with a radioactivity in the range of about 20 to 200 MBq (megabecquerels). When a radioactive complexing metal such as technetium-99 is used, the metal complex may be administered with a radioactivity in the range of about 350 to 1,000 MBq.

Hereinbelow, the present invention is further described and explained by way of examples which are specific embodiments of the present invention and should not be construed as limiting its scope.

EXAMPLE 1

Preparation of DTPA Monoethyl Monobenzylester 200 mmole of diethylene triamine pentaacetic acid (DTPA) bis anhydride (71.4 g) commercially available from Aldrich and 40 mmole dry triethylamine (TEA) in 1100 ml dry dimethylformamide were brought into solution at 50° C. To the warm solution were added 200 mmole ethanol and 200 mmole dry benzyl alcohol. After 2 hours reaction, solvents were removed under reduced pressure. The DTPA monoethyl monobenzylester was separated from the diethyl ester and the dibenzyl ester by preparative low pressure reversed phase liquid chromatography. Therefore, the residue was dissolved in 250 mM phosphate buffer ($H_3PO_4$/TEA at pH 6.5) and applied to a C18 silica column which was eluted with an acetonitrile gradient. High pressure liquid chromatography (210 nm monitoring, polymer column 4.6 mm×250mm, using a 25 mM phosphate/TEA buffer pH 6.5—acetonitrile gradient, 1 ml/min) showed that pure DTPA monoethyl monobenzyl ester eluted from the preparative column with 7.5% acetonitrile/buffer (25 mM $H_3PO_4$/TEA at pH 6.5) to 15% acetonitrile/water. Pure fractions were pooled and concentrated under reduced pressure. Subsequent desalting of the preparation was accomplished by preparative C18 column chromatography (elution with acetonitrile/water). Solvent from the desalted material was removed under reduced pressure. After removing excess water azeotropically with acetonitrile, the product was dried under vacuum over $P_2O_5$.

EXAMPLE 2

Preparation of DTPA Monoethyl Ester

DTPA monoethyl ester was prepared by hydrogenolysis of the purified compound obtained in example 1 by dissolving it in 350 ml of a 70% ethanol/30% water mixture (volume/volume), then adding 2 g palladium on activated carbon (Pd 10%). After 5 hours of a hydrogen gas treatment under a 20 p.s.i pressure, charcoal was removed by filtration over a thin path of Celite. The residue was then washed with the same warm ethanol/water mixture. Solvents from the combined filtrate and washings were removed under reduced pressure. Drying in vacuum over $P_2O_5$ afforded 27 g of DTPA monoethyl ester.

EXAMPLE 3

Preparation of DTPA Monoethyl Ester Mono Anhydride

The product of example 2 was converted to its mono anhydride derivative by means of the acetic anhydride/pyridine method, making use of 250 ml acetic anhydride and 42 ml pyridine under a nitrogen gas atmosphere. Finally, 14 g (34.7 mmole) of NMR-1H characterized (dimethylsulfoxide D6) DTPA monoethylester monoanhydride was obtained as a white powder.

EXAMPLE 4

Preparation of 3'-{[(2-alkyloxycarbonyl)-1H-indol-3-yl]-phenyl-methyl}-1H-indole-2-carboxylicacid ester The title compound was prepared from commercially available benzaldehyde and indole-2-carboxylic acid in a 90% yield, following the procedure disclosed by Gränacher et al. in *Helv. Chim. Acta* (1924) 7:579–586.

EXAMPLE 5

Preparation of (3'-{[(2-hydrazinocarbonyl)-1H-indol-3-yl]-phenyl-methyl}-1H-indole-2-carbonyl)-hydrazine 5 g (10.7 mmole) of the intermediate obtained in example 4 and 10.73 g hydrazine monohydrate are dissolved in a mixture of 60 ml pyridine and 30 ml methanol. After refluxing the mixture at 80° C. over night, solvents are removed under reduced pressure. The residue is treated by adding $H_2O$, $H_2O$/methanol and then acetonitrile; after each addition, the solvent is removed under reduced pressure. Finally, the hydrazide is precipitated from dichloromethane by the addition of acetonitrile, the precipitate is collected by filtration and dried over $P_2O_5$, yielding 3.4 g of the desired product. Identification thereof was confirmed by $^1$H- and $^{13}$C-NMR spectroscopy. Spectra are recorded on a Gemini 200 MHz spectrometer available from Varian (Palo Alto, Calif.). Chemical shifts are reported in ppm relative to tetramethylsilane (δ=0) as follows: $^1$H-NMR (DMSO) δ 4.51 (br s, NHNH2, 4H), 6.57–6.68 (m, ArH3, ArH4, 4H), 6.99–7.11 (m, ArH2, ArH, 4H), 7.21 (m, ArH, 3H), 7.27 (s, CH, 1H), 7.40 (d, ArH1, 2H), 9.62 (s, CONH, 2H), 11.40.

EXAMPLE 6

Preparation of the Bis-DTPA Amide of the Compound of Example 5 (First Method)

3 g (6.85 mmole) of the compound of example 5 is dissolved in 200 ml dry DMF containing 12 ml NN-diisopropylethyl amine. The monoanhydride of example 3 (6.6 g, 16.4 mmole) is added and the mixture is stirred until all starting hydrazide has disappeared. Completion of the reaction is monitored by reversed phase high performance liquid chromatography (HPLC) (gradient elution of a C8/5 μm column using 25 mM TRIS/HCl buffer pH 7.4 containing 0.5 mM EDTA and acetonitrile). Solvents are removed under reduced pressure. Protective ethyl ester groups are removed by dissolving the residue in diluted NaOH. A pH of 13.5 is maintained till all ethyl esters are hydrolyzed. After alkaline hydrolysis, the pH is adjusted to 7.0 and the sample

EXAMPLE 7

Preparation of the Bis-DTPA Amide of the
Compound of Example 5 (Second Method)

To a solution of DTPA-bisanhydride (21.5 g, 60 mmole) and triethylamine (35 ml) in 200 ml of dry dimethylformamide (DMF) was slowly added 1 ml of water (55 mmole) in 50 ml of dry DMF over a period of 2 hours. 20 mmole of the compound obtained in example 5 as then added and the reaction mixture was stirred overnight. After evaporation to dryness, the residue was dissolved at pH 8 (NaHCO$_3$ and 5N NaOH) and again evaporated to dryness to remove excess triethylamine. After dissolving the residue in 250 ml of 0.25M phosphate buffer pH 6.5 containing 2.5% of methanol, this solution was applied on a preparative C 18 column (1 kg) in the same buffer. The column was eluted with a decreasing gradient of buffer and increasing amounts of acetonitrile. Pure fractions were combined and evaporated to dryness, yield 75 g (containing phosphate salts). The product obtained was dissolved in 150 ml water and desalted on the same C 18 column in 2.5% of methanol, using a gradient of acetonitrile, yielding 28 g (44%) of the desired product. Its identification is confirmed by the following spectra data: $^1$H-NMR (D$_2$O) 3.0–3.8 (methylene hydrogens of DTPA, 18H); 6.8–7.6 (aromatic hydrogens and —CH, 14H). Identification was further confirmed by mass spectrometry on a Micromass LCT instrument (time of flight machine) with electrospray ionisation detection, yielding a peak at 579 (half of molecular mass, corresponding to a bisanionic compound at pH 7).

EXAMPLE 8

Preparation of the Bis Gadolinium Complex of the
Compound of Example 6

Gadolinium acetate was incrementally added to an aqueous solution of the compound of example 6. After each addition the pH was adjusted to 7.4 by means of NaOH (1.0 M). Formation of mono- and bis-gadolinium chelates was monitored by HPLC, knowing that chelation increases retention time. Addition of gadolinium acetate was stopped when the compound was virtually completely converted into the bis- and mono-gadolinium complexes, the latter amounting to minor amounts (DTPA moieties not involved in gadolinium complexation was less than 10%). Identity of the complex was confirmed by mass spectrometry on a Micromass LCT instrument (time of flight) with electrospray ionisation detection. Peaks are present at 1497 dalton (i.e. the molecular mass of the compound with single negative charge+Na) and at 748 dalton (i.e. half of that molecular mass, corresponding to the bis-anionic compound). Both peaks show the characteristic distribution of the different stable isotopes of gadolinium.

EXAMPLE 9

Preparation of 3'-{[(2-alkyloxycarbonyl)-1H-indol-3-yl]-methylene}-1H-indole-2-carboxylic acid ethyl ester.

The title compound was prepared from formaldehyde and indole-2-carboxylic acid in a 28% yield, following the procedure disclosed by Gränacher et al. in *Helv. Chim. Acta* (1924) 7:579–586.

EXAMPLE 10

Preparation of (3'-{[(2hydrazinocarbonyl)-1H-indol-3-yl]-methylene}-1H-indole-2-carbonyl)-hydrazine 7.35 g (20 mmole) of the intermediate obtained in example 10 and 30 ml hydrazine monohydrate are dissolved in a mixture of 100 ml pyridine and 30 ml methanol. After refluxing the mixture at 80° C. over night, solvents are removed under reduced pressure. The residue is treated by adding H$_2$O, H$_2$O/methanol then acetonitrile; after each addition, the solvent is removed under reduced pressure. Finally, the hydrazide is precipitated from dichloromethane by the addition of acetonitrile, the precipitate is collected by filtration and dried over P$_2$O$_5$, yielding 6.5 g of the desired product. Its identification is confirmed by the following spectra data: $^1$H-NMR (DMSO) δ 4.63 (br s, NHNH2, 4H), 4.92 (s, CH2, 2H), 6.81 (t, ArH2, 2H), 7.09 (t, ArH3, 2H), 7.33 (d, ArH4, 2H), 7.43 (d, ArH1, 2H), 9.52 (s, CONH, 2H), 11.12 (s, NH, 2H).

EXAMPLE 11

Preparation of [{2-[N'-(3-{[2-(N'-{2-[(2-{[2-bis(carboxymethyl-amino) -ethyl]carboxymethylsmino}-ethyl)carboxymethyl-amino]-acetyl}-hydrazinocarbonyl)-1H-indol-3-yl]-methylene}-1H-indole-2-carbonyl)-hydrazino]-2-oxo-ethyl}-(2-{[2-bis(carboxymethyl-amino)-ethyl]-carboxymethylamino}-ethyl)-amino]-acetic acid sodium salt Preparation was effected as described in example 6 but starting from 6.33 g of the compound of example 10, yielding the desired sodium salt in a 70% yield. Its identity was confirmed by mass spectrometry on a Micromass LCT instrument (time of flight machine) with electrospray ionisation detection, yielding a peak at 541 dalton, corresponding to the bisanionic compound at pH 7.

EXAMPLE 12

Preparation of the Bis Gadolinium Complex of [{2-[N'-(3-[{2-(N'-{2-[(2-{[2-bis(carboxymethyl-amino)-ethyl]carboxymethylamino}-ethyl)carboxymethyl-amino]-acetyl}-hydrazinocarbonyl)-1H-indol-3-yl]-methylene}-1H-indole-2-carbonyl)-hydrazino]-2-oxo-ethyl}-(2-{[2-bis(carboxymethyl-amino)-ethyl]-carboxymethylamino}-ethyl)-amino]-acetic acid sodium salt.

The compound of example 11 (12.0 g, 10 mmole) was dissolved in 200 ml water; a solution of 11.5 mmole of gadolinium acetate Gd(OAc)$_3$.3H$_2$O in 100 ml of water was then slowly added while maintaining the pH at 7 with 25% NH$_3$. The Gd-complex was evaporated to dryness, washed with acetonitrile and dried under vacuum over phosphorus pentoxide and sodium hydroxide for removing ammonium acetate. 13.25 g (90%) of the title complex was obtained. Its identity was confirmed by mass spectrometry on a Micromass LCT instrument (time of flight machine) with electrospray ionisation detection, yielding peaks at 711 dalton (corresponding to half of the molecular mass (bisanionic compound+Na)) and at 474, corresponding to ⅓ of that molecular mass for the tris-anionic compound. Both peaks show the characteristic distribution of the different stable isotopes of gadolinium.

EXAMPLE 13

Preparation of {4,7-Bis-carboxymethyl-10-[({3-[(2-{N'-[(4,7,10-tris-carboxymethyl-1,4,7,10-tetraazacyclododec-1-yl)-acetyl]-hydrazinocarbonyl}-1H-indol-3-yl)-phenyl-methyl]-1H-indole-2-carbonyl}-hydrazino)-2-oxo-ethyl]-1,4,7,10-tetraazacyclododec-1-yl}-acetic acid 1,4,7,10-tetraazacyclododecane tetraacetic acid (DOTA, 8.08 g, 20 mmole) was dissolved in a mixture of 15 ml of ammonia and 250 ml of dry DMSO by stirring and sonicating. O-(Benzotriazol-1-yl)-N,N,N',N'-tetramethyluronium tetrafluoroborate (TBTU, 9.63 g, 30 mmole) was added and allowed to react for 30 minutes. The compound of example 5 (2.63 g, 6 mmole) was then added and allowed to react for 60 minutes. High performance liquid chromatography (HPLC) on a RP-18 Chromolith column Merck (10 cm length) eluted with gradient mixtures of acetonitrile in 0.05 M ammonium phosphate buffer pH 6.8 (0 to 80% acetonitrile over a period of 30 minutes) showed that the reaction mixture contained a mixture of the mono- and bis-DOTA derivatives. Isolation of the bis-DOTA compound was carried out on a 1-kg RP-18 column, using as the eluent 10% ammonium acetate in 2.5% methanol, followed by 5% methanol and finally 10% methanol. The title compound was isolated from the appropriate fractions in a 40% yield (3.11 g). Its identity was confirmed by mass spectrometry on a Micromass LCT instrument (time of flight machine) with electrospray ionisation detection, yielding a peak at 616 dalton (corresponding to half of the molecular mass (bisanionic compound+Na).

EXAMPLE 14

Preparation of 3,3'-p-methoxybenzylidenebis(indole-2-carboxylic acid ethyl ester) or 3'-{[(2-alkyloxycarbonyl)-1H-indol-3-yl]-(4-methoxyphenyl)-methyl}-1H-indole-2-carboxylic acid ethyl ester The title compound was prepared, from 4-methoxybenzaldehyde and indole-2-carboxylic acid in a 85% yield, following the procedure disclosed by Gränacher et al. in *Helv. Chim. Acta* (1924) 7:579–586.

EXAMPLE 15

Preparation of (3'-{[(2-hydrazinocarbonyl)-1H-indol-3-yl]-(4-methoxyphenyl)-methyl}-1H-indole-2-carbonyl)-hydrazine Preparation was effected, starting from the compound of example 15, in a 80% yield, by using the procedure described in detail for example 5. Identification of the resulting compound is confirmed by the following spectra data: $^1$H-NMR (DMSO) δ 3.72 (s, OCH3, 3H), 4.53 (br s, NHNH2, 4H), 6.66 (m, ArH4, ArH3, 4H), 6.80 (d, ArH5, 2H), 6.91 (d, ArH6, 2H), 7.03–7.12 (m, ArH2, 2H), 7.18 (s, CH, 1H), 7.40 (d, ArH1, 2H), 9.59 (s, CONH, 2H), 11.39 (s, NH, 2H).

EXAMPLE 16

Preparation of [{2-[N'-(3-{[2-(N'-{2-[(2-{[2-bis(carboxymethyl-amino)-ethyl]carboxymethylamino}-ethyl)carboxymethyl-amino]-acetyl}-hydrazinocarbonyl)-1H-indol-3-yl]-(4-methoxyphenyl)-methyl}-1H-indole-2-carbonyl)-hydrazino]-2-oxo-ethyl}-(2-{[2-bis(carboxymethyl-amino)-ethyl]-carboxymethylamino}-ethyl)-amino]-acetic acid sodium salt.

Preparation starting from the compound of example 15 was effected essentially as described in example 6 above, providing the title compound in a 53% yield. The identity of the resulting compound was confirmed by the following spectra data: $^1$H-NMR (DMSO-D20) δ 3.1–3.8 (m, 36H, CH2), 3.68 (s, OCH3, 3H), 6.6–6.8 (m, ArH,6H), 6.99 (s, CH, 1H), 7.1–7.2 (m, 4H), 7.53 (d, ArH, 2H). Identity of the compound was further confirmed by mass spectrometry on a Micromass LCT instrument (time of flight machine) with electrospray ionisation detection, yielding a peak at 595 (half of molecular mass, corresponding to a bisanionic compound at pH 7).

EXAMPLE 17

Preparation of the bis gadolinium Complex of [{2-[N'-(3-{[2-(N'-{2-[(2-{[2-bis(carboxymethyl-amino)-ethyl]carboxymethylamino}-ethyl)carboxymethyl-amino]-acetyl}-hydrazinocarbonyl)-1H-indol-3-yl]-(4-methoxyphenyl)-methyl}-1H-indole-2-carbonyl)-hydrazino]-2-oxo-ethyl}-(2-{[2-bis(carboxymethyl-amino)-ethyl]-carboxymethylamino}-ethyl)-amino]-acetic acid sodium salt.

The compound of example 16 was quantitatively converted to its bis-gadolinium complex by following essentially the same procedure as described in example 8. Identity of the complex was confirmed by mass spectrometry on a Micromass LCT instrument (time of flight) with electrospray ionisation detection. Peaks are present at 763 dalton (half of the molecular mass, corresponding to the bis-anionic compound) and 508 dalton (one third of the molecular mass: compound with three negative charges). Both peaks show the characteristic distribution of the different stable isotopes of gadolinium.

EXAMPLE 18

Preparation of the indium-111 complex of [{2-[N'-(3-{[2-(N'-{2-[(2-{[2-bis(carboxymethyl-amino)-ethyl]carboxymethylamino}-ethyl)carboxymethyl-amino]-acetyl}-hydrazinocarbonyl)-1H-indol-3-yl]-(4-methoxyphenyl)-methyl}-1H-indole-2-carbonyl)-hydrazino]-2-oxo-ethyl}-(2-{[2-bis(carboxymethyl-amino)-ethyl]-carboxymethylamino}-ethyl)-amino]-acetic acid sodium salt In a 10-ml vial, 2.5 mg of the compound of example 6 is dissolved in 0.2 ml of a 0.1 molar citrate buffer pH 4.0. To this solution is added 0.4 ml of a [$^{111}$In] indium chloride solution (Tyco Healthcare, DRN 4901) containing 26 megabecquerel (MBq) of $^{111}$In. The solution is incubated for 30 minutes at 23° C. and then analysed by HPLC on an X-Terra RP18 column (250 mm×4,6 mm, particle size 5 μm), eluted with gradual mixtures of 0.1 molar ammonium acetate and acetonitrile (0% acetonitrile at start, linearly increased to 90% acetonitrile after 30 minutes). The eluate is monitored for radioactivity using a NaI(TI) scintillation detector and for UV absorbance using a UV-detector. The only peak of radioactivity elutes at 19.5 minutes, immediately after the UV-peak corresponding to the compound of example 6.

EXAMPLE 19

In vivo Test of Rat Liver Infarction

Adult Wistar rats (weighing between 300 and 400 g) were anesthetized with intraperitoneal injection of pentobarbital (Nembutal® available from Sanofi Santé Animale, 1130 Brussels, Belgium) at a dose of 40 mg/kg. Under laparotomy, reperfused hepatic infarction was induced by temporarily clamping the hilum of the right liver lobe for 3 hours. After reperfusion by declamping hepatic inflow, the abdominal cavity was closed with 2-layer sutures and the rats were left to recover for 8 to 24 hours after surgery.

Animals were anesthetized again as above for magnetic resonance imaging (MRI). The tail vein of the rat was cannulated with a G27 infusion set (available from Vicon, Belgium) connecting to a 1 ml tuberculin syringe loaded with a 43 mM Gd solution of the complex of example 8. The rat was imaged at 1.5 T scanner (Magnetom Vision, available from Siemens, Erlangen, Germany) within a cylindrical copper coil. T2-weighted (repetition time/echo time TR/TE=3000 ms/90 ms) and T1-weighted (TR/TE=420 ms/12 ms) spin echo sequences were applied. Other MRI parameters were as follows: slice thickness was 2 mm (without gap); the field of view was 7.5 cm×10 cm, with a matrix of 192×256. Two acquisitions were averaged, resulting in a measurement time of about 3 minutes. A glass tube containing 0.02% $CuSO_4$ solution was placed beside the rat as an external standard for normalization of signal intensity (SI) values. Together with a precontrast T1-w imaging, only one T2-w measurement was performed at the beginning to verify the presence of infarcted liver lobe. Rats were scanned on transverse sections before and after contrast injection of the compound of example 8 at a concentration of 0.05 mmole Gd per kg body weight. Postcontrast T1-w MRI was effected 5 minutes (early phase), 40 minutes and 24 hours (late phase) thereafter.

At the end of imaging studies, rats were sacrificed by an intravenous overdose of phenobarbital and placed in a deep freezer (below −20° C.) overnight in the same position as that during MR imaging. The frozen rats were sectioned in the transverse plane similar to that on MRI in order to match the imaging and histologic findings. Another approach was to perfuse freshly excercised liver (or other organs) with a 2,3,5-triphenylterazolium solution in order to provoke staining of viable tissue.

For the purpose of microscopy, tissue samples were fixated, sectioned, stained and analyzed according to standard procedures.

Figure 3:
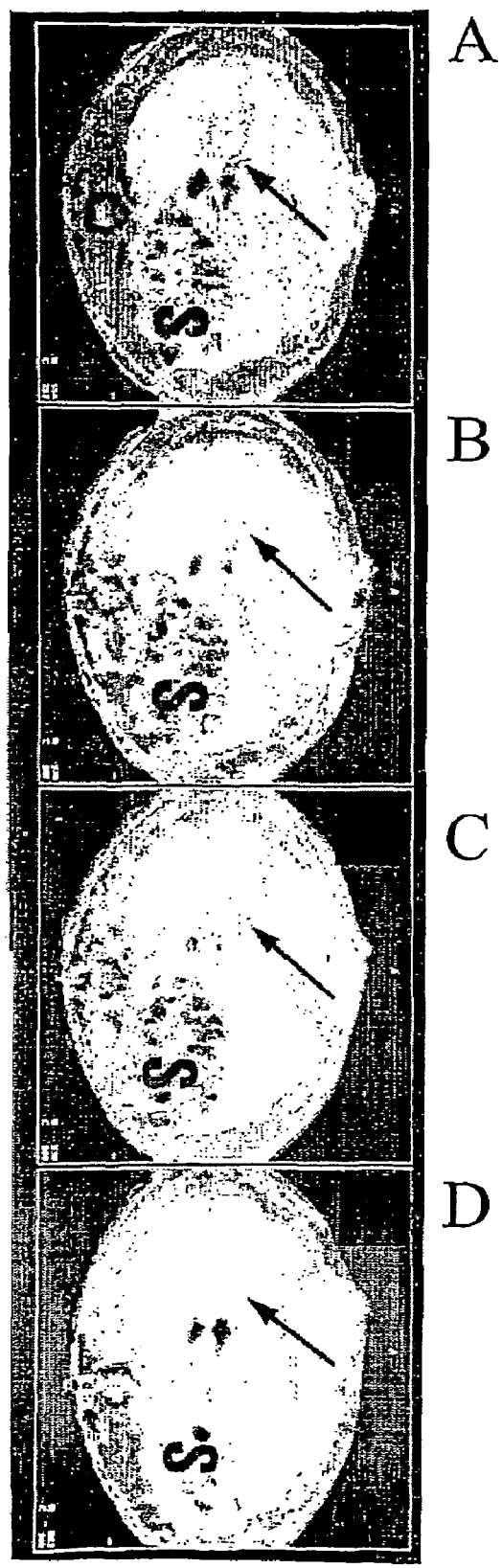
FIG. 3(A-D) illustrates the necrosis contrast agent function of one exemplary metal-complexable bis-indole derivative according to the invention by showing photographs of magnetic resonance images (MRI) obtained in a rat model of experimentally induced reperfused liver infarction before (A) and after (B-D) intravenous injection of the compound of examples 8.

Results of MRI-imaging and post mortem macroscopic analysis as shown in FIG. 3 (A-E) demonstrate the blood pool effects of the compound of example 8 and its ability to visualize necrosis. Before contrast, the infarcted liver lobe (arrow) is almost isointense relative to the normal liver (A). While immediately after (B) injection of the compound, the signal intensity of normal liver is enhanced and the infarcted lobe (arrow) remains hypointense. All intrahepatic vessels exhibit strong signal intensity, a feature characterizing the reperfused infarction model. 40 minutes later (C), the contrast between normal and infarcted liver is reversed due to a combination of events comprising (1) gradual contrast perfusion and diffusion into the necrotic lobe, (2) declining plasma concentrations (due to slow clearance fom the blood and elimination from the body) and (3) retention of the contrast agent in the necrosis by biospecific binding to necrotic tissue or components thereof. The simultaneous occurrence of these dynamic events cause heterogeneous contrast enhancement of necrosis in the early phase. 24 hours after administration (D), the signal intensity of both the normal liver and the vessels have largely decreased. However the infarcted lobe displays a persistent homogenous contrast enhancement, illustrating that the complex of example 8 exhibits necrosis-specificity. Comparison of the in vivo MR-image of FIG. 3D with post mortem histologic localisation of necrosis (FIG. 3E showing the necrotic tissue of a rat section corresponding to the MRI-slice of FIG. 3D), confirms that the observed late phase contrast enhancement exactly matches necrosis. Hence, the compound of example 8 has necrosis seeking ability and is useful for unambiguous identification and in vivo visualization of necrosis.

In addition, blood clearance of the compound of example 8 was slow (T1/2 is about 2.5 hours). In conjunction with its ability to reversibly bind to serum proteins, in particular to serum albumin, this means that it also exhibits bloodpool effects.

EXAMPLE 20

In Vivo Test of Rat Liver Infarction at Low Dose

The complex of example 8 (used in an appropriate dilution, by means of saline buffer, of a preparation of 350 mM Gd) was further tested in the same rat model of reperfused liver infarction as described in example 19 at both normal and low dose. One group of rats received a dose of about 50 μmole gadolinium per kg body weight (as in example 19) while the other group received a dose of about 10 μmole gadolinium per kg body weight. MRI-images and histologic correlation, performed under the same conditions as in example 19, demonstrated unambiguous enhancement of necrotic tissue even at a dose as low as 10 μmole Gd/kg. 24 hours after injection of the complex, the observed ratio between normal and necrotic liver was equal to or higher than 1.3 in rats who received the 10 μmole Gd/kg dose. In rats who received the 50 μmole Gd/kg dose, this ratio was greater than 1.6. Taking into account that the agent is cleared rather slowly and that normal liver is involved in eliminating the complex from the body, and that 24 hours after injection there is still enhancement in normal liver on MRI images, therefore when infarction is located in the myocardium or the brain, or more generally in organs and/or tissues not involved in elimination of the complex, the contrast ratio will be still much higher. Accordingly, doses below 15 μmole Gd/kg will be effective in vivo when the complex is used in systemic applications. When the site of necrosis permits local administration of the agent (such as for example intracoronary administration in the case of myocardial infarction), then doses far below those effective in systemic applications can be used.

EXAMPLE 21

In Vivo Test of Rat Liver Infarction with Delayed Administration

The compound of example 8 was further tested in the same rat model of reperfused liver infarction as described in example 8 at normal dose (about 50 µmole Gd/kg) and low dose (about 15 µmole Gd/kg), but administering the said compound after a delay of 48 hours following inducing the liver infarction. MRI-images and histologic correlation, performed under the same conditions as in example 19, revealed that even under such conditions, excellent enhancement of necrosis was obtained, i.e. the observed contrast ratios were similar as in examples 19 and 20.

EXAMPLE 22

Toxicity of a Gadolinium Complex

Possible toxic side effects of the complex of example 8 were studied in five normal Wistar rats that received a bolus intravenous injection of about 1,000 µmole Gd/kg. After treatment, rats were kept in standard conditions, having free access to water and food. Being carefully monitored during the first 10 hours after injection, they did not show any sign of abnormal behaviour. After 24 hours, the rats were sacrificed, organs were excised and macroscopically inspected. Tissue samples were collected and prepared for microscopic analysis. Post mortem inspection of organs did not reveal any abnormalities. Extensive microscopic analysis of tissue samples (liver, heart, kidney, brain and muscle) did not show any abnormal histology and did not reveal any histological indication of toxicity (such as e.g. inflamation, necrosis and the like).

EXAMPLE 23

In Vivo Test of Pig Myocardial Infarction

Pigs weighing about 40 kg were sedated with intramuscular xylazine (commercially available under the tradename Rompun from Bayer) at 2.5 ml/kg, anesthetized with an intravenous bolus of 60 mg of sodium pentobarbital (Nembutal, Sanofi), intubated and ventilated on a positive pressure ventilator. Anesthesia was maintained by dosed infusion of sodium pentobarbital beneath the level of spontaneous respiration. Myocardial infarction was induced through a surgical procedure. After left posterolateral thoracotomy and opening of the pericardium, the left coronary artery was identified and a loose snare loop with a 3–0 silk suture was applied around the artery and lead out of the chest through a small incision. The chest was closed after evacuation of the pneumothorax. After baseline imaging, obstructive myocardial infarction was induced by tightening of the snare through a 7 French latex tube for 150 to 180 minutes. The ischemic effect of the procedure was verified by electrocardiography (hereinafter referred as ECG) changes. Coronary perfusion was restored by subsequent removal of the occluder.

30 to 60 minutes after reperfusion, a dose of 0.05 mmole/kg of the compound of example 8 was administered intravenously. Cardiac MRI was performed one, two, four, six and twelve hours respectively after administration on a 1.5 T clinical imager (Siemens Magnetom Vision, Erlangen, Germany) with gradient switching capabilities of 25 mT/m in 300 µsec. All pigs were positioned in the supine position in the standard surface coil, centered on the xyphoid process of the sternum. MR images were obtained in the true short axis and optionally in the long-axis. Under ventilator-assisted breath-holding, we used an ECG-triggered and segmented single-slice turboFLASH sequence. The sequence starts by applying a 180° inversion pulse for annulling the signal from the cardiac cavity, after which an echo train of 33 echoes is acquired after each R-peak of the ECG. With a matrix of 165×256, this results in filling of k-space in 5 heartbeats. Other sequence parameters were: TR/TE/α: 7.5 msec/4.3 msec/25°, inversion of 600 ms. The field of view was 240×320 mm and the slice thickness 6 mm.

At the end of imaging study, the animals were sacrificed and the excised heart was stained in a solution of buffered triphenyltetrazolium chloride (hereinafter referred as TTC). TTC staining results in red coloration of non-infarcted tissue, whereas necrotic areas exhibit a pale color. All slices were photographed and digitized for morphometry.

Figure 4:
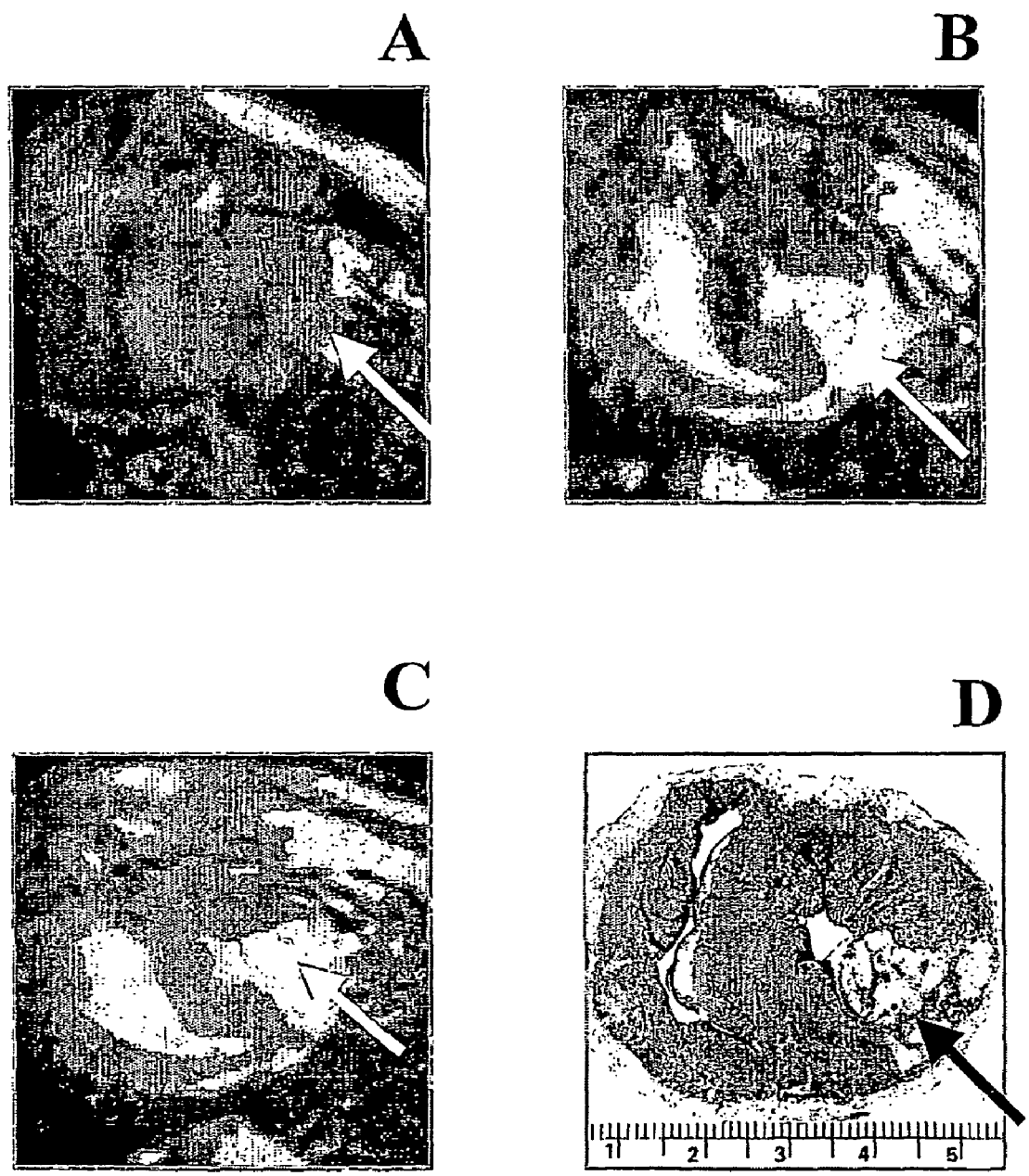
FIG. 4(A-C) illustrates the necrosis contrast agent function of one exemplary metal-complexable bis-indole derivative according to the invention by showing magnetic resonance images of a pig with reperfused myocardial infrarction before (A) and after (B-C) intravenous injection of the compound of example 8.

Results of MRI-imaging and post mortem macroscopic analysis as shown in FIGS. 4(A-D) demonstrate the effects of the compound of example 8. Before contrast, the infarct (arrow) appeared isointense and invisible (A). Respectively 2 hours (B) and 6 hours (C) after intravenous injection of the compound of example 8 at a dose of 0.05 mmole/kg, the signal intensity of infarct (arrow) was persistently enhanced. The pale infarcted region (arrow) on TTC histochemically stained section confirmed the above MRI finding (D).

EXAMPLE 24

(Comparative) and 25—Effect of in Vivo Intravenous Injection in a Rabbit

Figure 5:
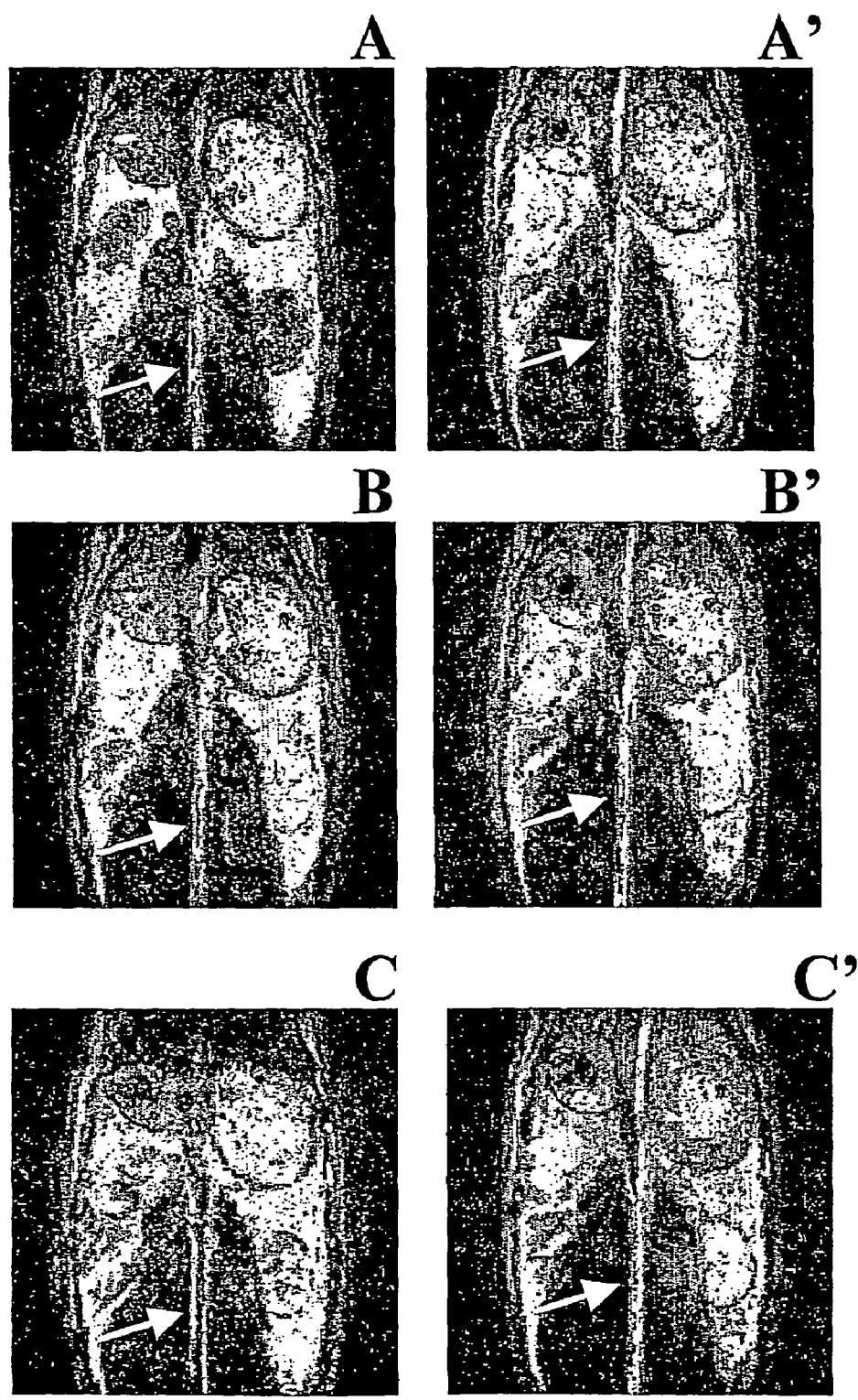
FIG. 5 shows magnetic resonance angiographic images of a rabbit after intravenous injection of a commercial contrast agent Gd-DTPA (A-C) as a comparative example, and (A'-C') after intravenous injection of one exemplary metal-complexable bis-indole derivative according to the invention (the compound of example 8).

For the purpose of a comparison with a known contrast agent, MR angiographic images of a rabbit were taken (shown in FIG. 5) after intravenous injection of:
- a commercial MRI contrast agent (Gd-DTPA commercially available under the tradename Magnevisto® from Schering A G, Berlin, Germany) at a concentration of 0.1 mmole per kg bodyweight (A-C), and
- the complex of example 8 at a concentration of 0.05 mmole per kg bodyweight (A'-C').

More specifically, immediately after Gd-DTPA injection, the abdominal aorta (arrow) was moderately enhanced by the first pass of the contrast agent (A). One minute after contrast, the aorta (arrow) could only be faintly enhanced (B). Six minutes after contrast, the aorta was on longer enhanced as a result of complete washout of the agent from the blood circulation (C). By contrast, during the first pass immediately after intravenous injection, the complex of example 8 caused a stronger contrast enhancement of the abdominal aorta (arrow) (A'). Furthermore, the induced vascular contrast enhancement (arrow) persisted over 20 minutes (B') through 70 minutes (C') after contrast.

EXAMPLE 26

In Vivo Tests in a Rat Model of Liver Metastasis

Under the same general anaesthesia procedure as in example 19, the liver of Wistar rats was implanted with a cube (1×1×1 mm$^3$) of freshly harvested R1 rhabdomyosarcoma tissue. One week after implantation, the tumor size grew to 0.8–1.2 cm in diameter, ready for radiofrequency ablation (RFA). The RFA protocol was as follows: after anaesthesia, an incision was made along the primary incision for tumor implantation. Under visual inspection, an 18

Gauge cool-tip electrode (Radionics, Burlington, Mass., USA) was directly inserted into the liver tumor. Radiofrequency current was delivered from a RF generator (RFG-3E, available from Radionics) under power control mode at 30W for 20–30 seconds depending on the size of the tumor. The ablation volume covered both the entire tumor and a 3–5 mm rim of peritumoral liver parenchyma. After RFA, the electrode was withdrawn and the incision closed. The efficacy of the therapy was evaluated with contrast enhanced MRI, using the compound of example 8 at a concentration of 0.05 mmole per kg bodyweight, and histopathology.

Figure 6:
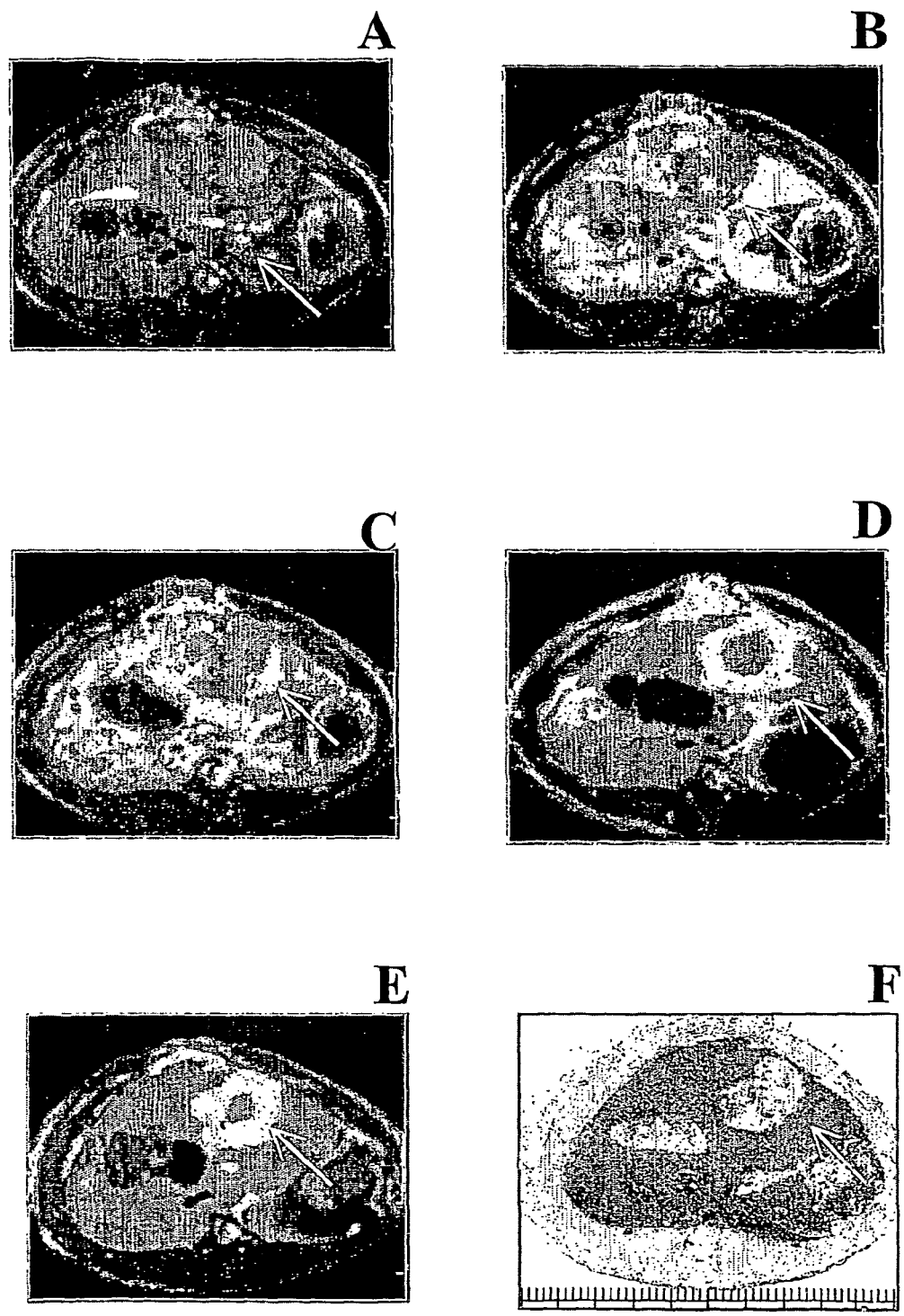
FIG. 6(A-E) shows magnetic resonance images of a rat with liver implantation of rhabdomyocarcoma treated with radiofrequency ablation before (A) and after (B-E) intravenous injection of one exemplary metal-complexable bis-indole derivative according to the invention (the compound of example 8).

Results of MR images (A-E) and cross section (F) of a rat with liver implantation of rhabdomyocarcoma treated with radiofrequency ablation, as shown in FIG. 6(A-F), demonstrate the effects of the compound of example 8. Before contrast, the treated tumor (arrow) appeared isointense and invisible (A). Respectively 1 minute (B) and 10 minutes (C) after intravenous injection of the compound of example 8 at a dose of 0.05 mmole per kg body weight, the signal intensity of liver is moderately enhanced leaving the lesion (arrow) as a spherical hypointense region. Respectively 6 hours (D) and 24 hours (E) after contrast, when the liver returned to its normal signal intensity, the lesion (arrow) including the ablated tumor and a layer of surrounding necrotic liver tissue showed a striking rim contrast enhancement, suggesting a complete tumor eradication. The pale necrotic region (arrow) apparent on the histological section (F) confirmed the above MRI finding.

EXAMPLE 27

Preparation of indole-3-carboxylic acid ethyl ester

The title compound is prepared starting from indole-3-carboxylic acid (commercially available from Aldrich) by esterification with ethanol using standard methods of organic synthesis (e.g. J. March, *Advanced Organic Chemistry, Reactions, Mechanisms and Structure* (1992, 4$^{th}$ edition) 393–394 (Wiley interscience, New York).

EXAMPLE 28

Preparation of 2'-[(3carboxyethyl-1H-indole-2yl)-phenyl-methyl]-1H-indole-3-carboxylic acid ethyl ester The title compound is prepared starting from benzaldehyde and from the compound of example 27, using the method described in example 4.

EXAMPLE 29

Preparation of the bis-hydrazide of 2'-[(3-carboxyethyl-1H-indole-2yl)-phenyl-methyl]-1H-indole-3-carboxylic acid The title compound is prepared from the compound of example 28 using the method described in example 5.

EXAMPLE 30

Preparation of the Bis DTPA Conjugate with the bis-hydrazide of 2'-[(3-carboxy-1H-indole-2yl)-phenyl-methyl]-1H-indole-3-carboxylic acid The title compound is prepared from the compound of example 29 using the method described in example 6.

EXAMPLE 31

Preparation of the bis-gadolinium Complex of [{3-[N'-(2-{[3-(N'-{2-[(2-{[2-bis(carboxymethyl-amino)-ethyl]carboxymethylamino}-ethyl)carboxymethyl-amino]-acetyl}-hydrazino-carbonyl)-1H-indol-2-yl]-phenyl-methyl}-1H-indole-3carbonyl)-hydrazino]-2-oxo-ethyl}-(2-{[2-bis(carboxymethyl-amino)-ethyl]-carboxymethylamino}-ethyl)-amino]-acetic acid sodium salt.

The title compound is prepared from the compound of example 30 using he method described in example 8.

EXAMPLE 32

Preparation of 2'-[2-(3-carboxyethyl-1H-indole-2-yl)-ethylene]-1H-indole-3'-carboxylic acid ethyl ester The title compound is prepared starting from 2'-[2-(3-carboxy-1H-indole-2-yl)-ethyl]-1H-indole-3'-carboxylic acid (the latter being prepared following the procedure described by D. Nagarathnanet al. in *Ind. J. Chem.* (1981) 20B, 796–797, by esterification with ethanol using standard methods of organic synthesis (e.g. J. March cited supra).

EXAMPLE 33

Preparation of the dihydrazide of 2'-[2-(3-carboxyethyl-1H-indole-2-yl)-ethylene]-1H-indole-3'-carboxylic acid The title compound is prepared from the compound of example 32 using the method described in example 5.

EXAMPLE 34

Preparation of the bis-DTPA Conjugate of the dihydrazide of 2'-[2-(3-carboxyethyl-1H-indole-2-yl)-ethylene]-1H-indole-3'-carboxylic acid The title compound is prepared from the compound of example 33 using the method described in example 6.

EXAMPLE 35

Preparation of the bis-gadolinium Complex of the bis-DTPA Conjugate of the dihydrazide of 2'-[2-(3-carboxyethyl-1H-indole-2-yl)-ethylenel-1H-indole-3'-carboxylic acid The title compound is prepared from the compound of example 34 using the method described in example 8.

EXAMPLE 36

Preparation of the bis-hydrazide of 3'-(2-carboxy-1H-indole-3-ylsulfanyl)-1H-indole-2'-carboxylic acid The title compound is prepared starting from 3'-(2-carboxyethyl-1H-indole-3-ylsulfanyl)-1H-indole-2'-carboxylic acid ethyl ester (the latter being prepared following the procedure described by J. Szmuszkovicsz, *J. Org. Chem.*

(1964) 29: 178–184), by esterification with ethanol using standard methods of organic synthesis (e.g. J. March cited supra)

EXAMPLE 37

Preparation of the bis-DTPA Conjugate of the bis-hydrazide of 3'-(2-carboxy-1H-indole-3-ylsulfanyl)-1H-indole-2'-carboxylic acid The title compound is prepared from the compound of example 36 using the method described in example 6.

EXAMPLE 38

Preparation of the bis-gadolinium Complex of the bis-DTPA Conjugate of the bis-hydrazide of 3'-(2-carboxy-1H-indole-3-ylsulfanyl)-1H-indole-2'-carboxylic acid The title compound is prepared from the compound of example 37 using the method described in example 8.

EXAMPLE 39

Preparation of the bis-DTPA Conjugate of 2'-(3-(2-aminoethyl)-1H-indole-2-ylsulfanyl)-1H-indole-3'-ethyl-2-amine The title compound is prepared from dithio-2,2'-ditryptamine (the latter being obtained following the procedure described by Barbier et al. in *J. Heterocycl. Chem.* (1989) 26:265–267), using the method described in example 6.

EXAMPLE 40

Preparation of the Bisgadolinium Complex of the bis-DTPA Conjugate of 2'-(3-(2-aminoethyl)-1H-indole-2-ylsulfanyl)-1H-indole-3'-ethyl-2-amine The title compound is prepared from the compound of example 39 using the method described in example 8.

EXAMPLE 41

Preparation of 2'-(3-(2-ethylcarboxyethyl)-1H-indole-2-ylsulfanyl)-1H-indole-3'-propionic acid ethyl ester The title compound is prepared starting from 3'-[2-(3-(2-carboxyethyl)-1H-indole-2-ylsulfanyl)-1H-indol-3'-yl]-propionic_acid (the latter being obtained following the procedure disclosed by Thompson et al., *J. Med. Chem.* (1994) 37(5):598–609 and U.S. Pat. No. 5,464,861) by esterification with ethanol using standard methods of organic synthesis (e.g. J. March cited supra)

EXAMPLE 42

Preparation of the bis-hydrazide of 3'-[2-(3-(2-ethylcarboxyethyl)-1H-indole-2-ylsulfanyl)-1H-indol-3'-yl]-propionic acid The title compound is prepared from the compound of example 41 using the method described in example 5.

EXAMPLE 43

Preparation of the bis-DTPA Conjugate of the bis-hydrazide of 3'-[2-(3-(2-ethylcarboxyethyl)-1H-indole-2-ylsulfanyl)-1H-indol-3'yl-]-propionic acid The title compound is prepared from the compound of example 42 using the method described in example 6.

EXAMPLE 44

Preparation of the bis-gadolinium Complex of the bis-DTPA Conjugate of the bis-hydrazide of 2'-(3-(2-ethylcarboxy)-1H-indole-2-ylsulfanyl)-1H-indole-3'-propionic acid The title compound is prepared from the compound of example 43 using the method described in example 8.

What is claimed is:

1. A substituted bis-indole derivatives of formula (I) or a mental complex, wherein said metal complex consisting of bis-indole derivatives of formula (I) and a radioactive or non-radioactive metal ion of an element with an atomic number selected from the group consisting of 21 to 32, 37 to 39, 42 to 44, 49, 50 or 57 to 83, and wherein the formula (I) is hereunder:

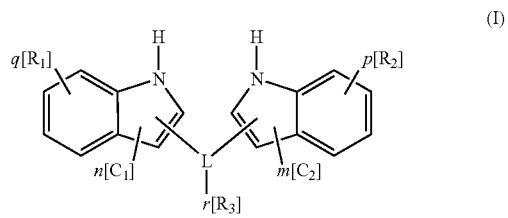

a pharmaceutically acceptable salt thereof wherein:
  L represents a single bond or an optionally substituted linking agent (Li) which covalently links together the carbon atoms being respectively in positions 2 or 3 and 2' or 3' on the heterocyclic indole rings, (Li) being an optionally substituted alkylene group;
  $R_1$ and $R_2$ are optional substituents of any free position of the phenyl rings of the indolyl groups and are each independently selected from halogen atoms, straight chain alkyl groups of 1 to 6 carbon atoms, branched chain alkyl groups of 3 to 7 carbon atoms, cycloalkyl groups of 3 to 7 carbon atoms, alkoxy groups of 1 to 6 carbon atoms, nitro, trifluoromethyl, cyano, carboxylic acid, sulfonic acid, carboxylic acid esters wherein the ester group derives from an alkyl group having 1 to 4 carbon atoms, substituted or unsubstituted carboxamides CO—$NR_4R'_4$ and substituted or unsubstituted amines $NR_4R'_4$ wherein $R_4$ and $R'_4$ are each independently selected from hydrogen and optionally substituted $C_1$–$C_{20}$ branched chain or straight chain alkyl groups or $C_6$–$C_{20}$ aryl groups or $C_6$–$C_{20}$ alkylaryl groups;
  $R_3$ is an optional substituent of the linking agent (Li) and is selected from optionally substituted aryl groups and optionally substituted branched chain or straight chain alkyl groups;

q, p and r are integers indicating the number of the respective substituents $R_1$, $R_2$ and $R_3$ and are each independently selected from 0 to 4, provided that r is 0 when L is a single bond;

$C_1$ and $C_2$ are metal chelating agent-containing substituents of the heterocyclic rings of the indolyl groups;

m and n are integers indicating the number of the respective metal chelating agent-containing substituents $C_1$ and $C_2$ and are each 0 or 1, provided that the sum of m and n is at least 1; and wherein $R_1$, $R_2$ or $R_3$ independently does not represent a heterocycle or heteroaryl, and wherein $R_1$, $R_2$ or $R_3$ independently is not substituted with a heterocycle or heteroaryl.

2. The bis-indole derivative or a metal complex according to claim 1, wherein m is 1 and n is 1.

3. The bis-indole derivative or a metal complex according to claim 1, wherein the substituent(s) on the aryl group $R_3$ are independently selected from the group consisting of halogen atoms, saturated or unsaturated hydrocarbon groups having 1 to 4 carbon atoms, alkoxy groups having 1 to 4 carbon atoms, cyano, carboxylic acid, sulfonic acid, carboxylic acid esters wherein the ester group derives from an alkyl group having 1 to 4 carbon atoms, substituted or unsubstituted carboxamicies $CO-NR_4R'_4$ and substituted or unsubstituted amines $NR_4R'_4$ wherein $R_4$ and $R'_4$ are each independently selected from the group consisting of hydrogen, optionally substituted $C_1-C_2$ branched chain or straight chain alkyl groups, $C_6-C_{20}$ aryl groups and $C_6-C_{20}$ alkylaryl groups.

4. The bis-indole derivative or a metal complex according to claim 1, wherein each of $C_1$ and $C_2$ is independently represented by the formula -(Sp)$_s$-CA, wherein (Sp) is a Spacing agent, s is an integer selected from 0 and 1, and CA is a chelating agent.

5. The bis-indole derivative or a metal complex according to claim 1, wherein each of $C_1$ and $C_2$ is independently represented by the formula -(SP)$_s$-CA, wherein CA is a chelating agent wherein a is 1 and wherein (Sp) is a spacing agent represented by the formula —(X)$_t$-(Sp')-, wherein (Sp') is a molecule bearing at one end a first functional group (i) suitable for reacting with a carboxylle acid function or with a primary or secondary amine and at the other end a second functional group (ii) suitable for reacting with the chelating agent CA, t is 0 or 1 and X is a carbonyl group or a secondary amino group.

6. The bis-indole derivative or a metal complex according to claim 1, wherein each of $C_1$ and $C_2$ is independently represented by the formula -(SP)$_s$-CA, wherein (Sp) is a spacing agent selected from the group consisting of bisamino and amino-acids, s is an integer selected from 0 and 1, and CA is a chelating agent.

7. The bis-indole derivative or a metal complex according to claim 1, wherein each of $C_1$ and $C_2$ is independently represented by the formula -(Sp)$_s$-CA, wherein (Sp) is a spacing agent, s is an integer selected from 0 and 1, and CA is a chelating agent comprising carboxymethyl groups —$CH_2COOR_4$ wherein $R_4$ is selected from the group consisting of hydrogen and optionally substituted $C_1-C_{20}$ branched chain or straight chain alkyl groups or $C_6-C_{20}$ aryl groups or $C_5-C_{20}$ alkylaryl groups.

8. The bis-indole derivative or a metal complex according to claim 1, wherein each of $C_1$ and $C_2$ is independently represented by the formula -(Sp)$_s$-CA, wherein (Sp) is a spacing agent, s is an integer selected from 0 and 1, and CA is a chelating agent comprising one or more moieties selected from the group consisting of bisamine-bisthiol, bisamine-bisoxime, monomercapto-triamide, diamide-dithiol, monoamine-monoamide-dithiol tetramine, monoamine-diamide-monothiol monoamine-monothboether-dithiol, monoamine-monothiol, monoamide-diamine-monathiol and diphosphine based moieties.

9. The bis-indole derivative or a metal complex according to claim 1, wherein each of $C_1$ and $C_2$ is independently represented by the formula -(Sp)$_s$-CA, wherein (Sp) is a spacing agent, s is an integer selected from 0 and 1, and CA is a chelating agent selected from the group consisting of ethylenediaminetetraacetic acid (EDTA), diethylene triaminopentaacetic acid (DTPA), trans-1,2-cyclohexanediamine tetraacetic acid (CDTA), 1,4,7,10-tetreaza-cyclododecane tetraacetic acid (DOTA), 1,4,7-triazacyclononanetriacetic acid, 1,4,8,11-tetraazacyclotetra-decane tetraacetic acid (TETA), ethyleneglycol-O,O'-bis(2-aminoethyl)-tetraacetic acid (EGTA), N,N-bis(hydroxybenzyl)ethylene-diamine-N, N'-diacetic acid (HBED), triethylene-tetramine hexaacetic acid (TTHA), hydroxyethyldiamine triacetic acid (HEDTA), 1,5,9-triazacyclo-dodecanetriacetic acid, and analogues thereof.

10. The bis-indole derivative or a metal complex according to claim 1, wherein each of $C_1$ and $C_2$ is independently represented by the formula -(SP)$_s$-CA, wherein (Sp) is a spacing agent, s is an integer selected from 0 and 1, and CA is a chelating agent selected from the group consisting of mercaptoacetyl triglycine, hexamethylpropylene diamine dioxime, ethylene dicysteine, ethylene cysteine cysteamine, cysteinylglycine cysteine, bismercaptoacetyl-diaminopropionic acid, bismercaptoacetyldiaminosuccinic acid, N-(mercaptoacetyl-aminoethyl)cysteine dimercaptosuccinic acid, dimercapto-propionic acid, cysteine, cysteamine, diphosphinopropionic acid, and derivatives thereof wherein one or more thiol functions are protected by a $R_4$ group, $R_4$ being selected from hydrogen and suitable thiol protective groups.

11. The bis-indole derivative or a metal complex according to claim 1, having the structure shown in formula (Ia) hereunder

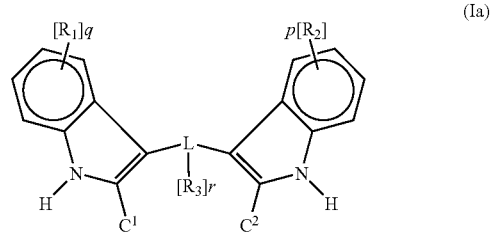

(Ia)

wherein L, $C_1$, $C_2$, $R_1$, $R_2$, $R_3$, p, q and r are as defined in claim 1.

12. The bis-indole derivative or a metal complex according to claim 1, being selected from the group consisting of:

[{2-[N'-(3-{[2-N'-{2-[(2-{[2-bis(carboxymethylamino)-ethyl]carboxymethyl-amino}ethyl)carboxymethylamino]-acetyl}hydrazinocarbonyl)-1H-indol-3-yl]-phenyl-methyl}-1H-indole-2-carbonyl)-hydrazino]-2-oxo-ethyl}-(2-{[2-bis(carboxymethyl-amino)-ethyl]-carboxymethylamino}-ethyl)-amino]-acetic acid, -[{2-[N'-(3-{[2-(N'-{2-[(2-{[2-bis(carboxymethyl-amino)-ethyl]carboxymethyl-amino]-ethyl)carboxymthyl-amino]-acetyl}-hydrazinocarbonyl)-1H-indole-3-yl]-methyl}-1H-indole-2-carbonyl)-hydrazino]-2-oxo-ethyl}-(2-{[2-bis(carboxymentyl-amino)-ethyl]-carboxymethylamino}-ethyl)-amino]-acetic acid, -{4,7-bis-carboxymethyl-10-[({3-[(2-{N'-[(4,7,10-tris-carboxymethyl-1,4,7,10-tetraaza-cyclododec-1-yl)-acetyl]-hydrazinocarbonyl}-1H-indol-3-yl)-methyl]-1H-indole-2-carbony}-hydrazino)-2-oxo-ethyl]-1,4,7,10-tetraaza-cyclododec-1-yl}-acetic acid, and -{4,8-bis-carboxymethyl-11-[({3-[(2-{N'-[(4,8,11-tris-caboxymethyl-1,4,8,11-tetraaza-cyclotetradec-1-yl)-acetyl]-hydrazinocarbonyl}-1H-indole-3-yl)-methyl]-1H-indol-2-carbonyl}-hydrazino)-2-oxo-ethyl]-1,4,8,11-tetraaza-cyclotetradec-1yl}-acetic acid,
enantiomers and pharmaceutically acceptable salts thereof.

13. The bis-indole derivative or a metal complex according to claim 1, being the sodium salt of [{2-[N'-(3-{[2-(N'-{2-[(2-{[2-bis(carboxymethylamino)-ethyl]carboxymethyl-amino}ethyl)carboxymethyl-amino]-acetyl}hydrazinocarbonyl)-1H-indol-3-yl]-phenyl-methyl}-1H-indole-2-carbonyl)-hydrazino]-2-oxo-ethyl}-(2-55[2-bis(carboxymethyl-amino)-ethyl]-carboxymethylamino}-ethyl)-amino]-acetic acid.

14. The bis-indole derivative or a metal complex according to claim 1, being the sodium salt of {4,7-bis-carboxymethyl-10-[({3-[(2-{N'-[(4,7,10-tris-carboxymethyl-1,4,7,10-tetraaza-cyclododec-1-yl)-acetyl]-hydrazinocarbonyl}-1H-indol-3-yl)-methyl]-1H-indole-2-carbonyl}-hydrazino)-2-oxo-ethyl]-1,4,7,10-tetraaza-cyclododec-1-yl}acetic acid.

15. the A bis-indole derivative or a metal complex according to claim 1, the said metal being a radioactive metal selected from the group consisting of $^{99m}$Tc, $^{111}$In, $^{67}$Ga, $^{90}$Y, $^{186}$Re and $^{188}$Re.

16. The bis-indole derivative or a metal complex according to claim 1, the said metal being a non-radioactive metal selected from the group consisting of gadolinium, manganese and iron.

17. A pharmaceutical composition comprising at least one pharmaceutically acceptable carrier and a substituted bis-indole derivative of formula (I) or a metal complx, wherein said metal complex consisting of bis-indole dervatives of formula (I) and a radioactive or non-radioactive metal Ion of an element with an atomic number selected from the group consisting of 21 to 32, 37 to 39, 42 to 44, 49, 50 or 57 to 83, and wherein the formula (I) is hereunder:

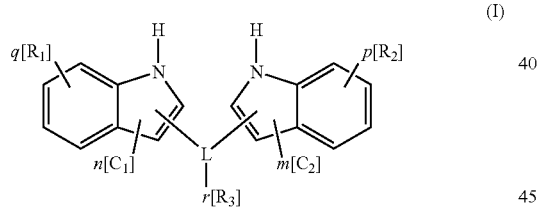

(I)

an enantiomer or a pharmaceutically acceptable salt thereof, or wherein:

L represents a single bond or an optionally substituted linking agent (Li) which covalently links together the carbon atoms being respectively in positions 2 or 3 and 2' or 3' on the heterocyclic indole rings, (Li) being an optionally substituted alkylene group;

$R_1$ and $R_2$ are optional substituents of any free position of the phenyl rings of the indolyl groups and are each independently selected from halogen atoms, straight chain alkyl groups of 1 to 6 carbon atoms, branched chain alkyl groups of 3 to 7 carbon atoms, cycloalkyl groups of 3 to 7 carbon atoms, alkoxy groups of 1 to 6 carbon atoms, nitro, trifluoromethyl, cyano, carboxylic acid, sulfonic acid, carboxylic acid esters wherein the ester group derives from an alkyl group having 1 to 4 carbon atoms, substituted or unsubstituted carboxamides CO—$NR_4R'_4$ and substituted or unsubstituted amines $NR_4R'_4$ wherein $R_4$ and $R'_4$ are each independently selected from hydrogen and optionally substituted $C_1$–$C_{20}$ branched chain or straight chain alkyl groups or $C_6$–$C_{20}$ aryl groups or $C_6$–$C_{20}$ alkylaryl groups, $R_3$ is an optional substituent of the linking agent (Li) and is selected from optionally substituted aryl groups and optionally substituted branched chain or straight chain alkyl groups;

q, p and r are integers indicating the number of the respective substituents $R_1$, $R_2$ and $R_3$ and are each independently selected from 0 to 4, provided that r is 0 when L is a single bond; p1 $C_1$ and $C_2$ are metal chelating agent-containing substituents of the heterocyclic rings of the indolyl groups;

m and n are integers indicating the number of the respective metal chelating agent-containing substituents $C_1$ and $C_2$ and are each 0 or 1, provided that the sum of m and n is at least 1; and wherein $R_1$, $R_2$ or $R_3$ independently does not renresent a heterocycre or heteroaryl, and wherein $R_1$, $R_2$ or $R_3$ independently is not substituted with a heterocycle or heteroaryl.

* * * * *